(12) United States Patent
Jacobs

(10) Patent No.: US 6,565,853 B1
(45) Date of Patent: May 20, 2003

(54) RECOMBINANT VIRUS

(75) Inventor: Susan C Jacobs, Salisbury (GB)

(73) Assignee: The Secretary of State for Defence in Her Britannic Majesty's Government of the United Kingdom of Great Britain and Northern Ireland, Hampshire (GB)

( * ) Notice: Subject to any disclaimer, the term of this patent is extended or adjusted under 35 U.S.C. 154(b) by 0 days.

(21) Appl. No.: 09/646,970

(22) PCT Filed: Mar. 19, 1999

(86) PCT No.: PCT/GB99/00874

§ 371 (c)(1),
(2), (4) Date: Oct. 23, 2000

(87) PCT Pub. No.: WO99/50292

PCT Pub. Date: Oct. 7, 1999

(30) Foreign Application Priority Data

Mar. 27, 1998 (GB) .............................................. 9806525
Nov. 17, 1998 (GB) .............................................. 9825053

(51) Int. Cl.[7] ...................... A61K 39/295; A61K 39/12; A61K 39/193; C12Q 1/70; C12Q 1/68; C12N 15/00; C07H 21/04

(52) U.S. Cl. ................................ 424/202.1; 424/204.1; 424/218.1; 424/233.1; 435/5; 435/6; 435/320.1; 536/23.1

(58) Field of Search ........................... 424/202.1, 204.1, 424/218.1, 233.1; 435/5, 6, 320.1; 536/23.1

(56) References Cited

U.S. PATENT DOCUMENTS 5,185,440 A  2/1993  Davis et al.

FOREIGN PATENT DOCUMENTS

WO     98/530771     11/1998

OTHER PUBLICATIONS

Kinney et al. 1988. Recombinant vaccinia virus/Venezuelan Equine Encephalitis (VEE) virus expresses VEE structural proteins. Journal of Virology. 68(69); 3005–3013.*

Forsell et al. 1995. Structure –function relation of the NH2–terminal domain of the Semliki Forest Virus capsid protein. Journal of Virology. 69(3); 1556–1563.*

Jakob R.: "Nucleolar accumulation of core protein in cells naturally infected with Semliki Forest virus" Virus Research, (1993) vol. 30, No. 2, pp. 145–160.

Kinney R. M. et al.: "The Full–Length Nucleotide Sequences of the Virulent Trinidad Donkey Strain of Venezuelan Esquire Encephalitis Virus and Its Attenuated Vaccine Derivative, Strain TC–83" Virology, (1989) vol. 170, No. 1, pp. 19–30.

Kuhn R. et al.: "Attenuation of Sindbis Virus Neurovirulence by Using Defined Mutations in Nontranslated Regions of the Genome RNA" Journal of Virology, (1992) vol. 66, No. 12, pp. 7121–7127.

* cited by examiner

*Primary Examiner*—James Housel
*Assistant Examiner*—Shanon Foley
(74) *Attorney, Agent, or Firm*—Nixon and Vanderhye

(57) ABSTRACT

An adenovirus which encodes a polypeptide which produces a protective immune response against an alpha-virus such as a Venezuelan Equine Encephalitis Virus, in a mammal to which it is administered, said nucleic acid lacking a competent nuclear targeting signal in the capsid gene.

23 Claims, 29 Drawing Sheets

Fig.2a.

L1  CTAGAGAATTCT
          TCTTAAGAGATC

XbaI   EcoRI   XbaI

Fig.2b.

L4A  CTAGTGACA*T*GG*T*GAATTCACCA*T*GTCA
         ACTGT*A*CCACTTAAGTGGT*A*CAGTGATC

SpeI *START* Kozak EcoRI Kozak *START* SpeI
        ∧                              ∧
   3 nt of 5' of E1              3 nt of 5' of E1

Fig.2c.

L7L8  GATCC*GTATA*TCTAGAGCATG
           *GCATAT*AGATCTC

BamHI   *AccI*   XbaI   SphI

Fig.2d.

L5L6  ATACTCCGGAGAACTGCGAGCAA*TGG*TAAT
          *TGA*GGCCTCTTGACGCTCGT*TACCATT*AGATC

AccI         3' Core         *STOP* XbaI

Fig.2e.

L10L13  *T*TAATCTAGAAGATGCA
        ACGTA*ATTAGATCTTCT*

NsiI *STOP* XbaI *Start* NsiI

Fig.2f.

L28L29 TGAGGGGCCATCCGCT AACAAGAAACCAGGCAAGAGACAGC..
       CCCCGGTAGGCGA TTGTTCTTTGGTCCGTTCTCTGTCG

<u>Bsu 36I</u>  nt7735-7750--Λ--  nt7886-8024

..GCATGGTCATGAAATTG*G*
  CGTACCAGTACTTTAAC*CTTA*

*Tfi*I

Fig.2g.

L30L31 ATACTCCGGAGAACTGCGAGCAATGGT*CACTAGTA*
       TGAGGCCTCTTGACGCTCGTTACCA*GTGATCATTGCA*
                                    --Λ--

<u>Acc</u>I      Core             E3  *Spe*I  HindIII

Fig.2h.

P2  GGCC*GGATCC*GGATGTTCCCGTTCCAGCC

<u>GC Rich tail</u> *Bam*HI    Start  5' Core

Fig.2i.

P3  GCGC*GGATCC*CCTCAGGTGGCGCG

<u>GC Rich tail</u> *Bam*HI  Bsu 36I  Core

Fig.2j.

L20  <u>GCGCCA</u>  *CTGAGGGGCCATCGC*

<u>GC Rich tail</u> *Bsu 36I*  5' Nuclear targeting signal

Fig.2k.

L21  <u>CGGG</u>*GATT*CTGGTTTCTTGTTGGTCTTCTTCTTG

<u>GC Rich tail</u> *Tfi*I  3' Nuclear targeting signal

RECOMBINANT VIRUS

The present invention relates to the production of vectors which express alpha-virus genes, such as recombinant viral vectors like adenovirus. The invention further relates to prophylactic and therapeutic vaccines which are protective against these alpha-viruses, such Venezuelan Equine Encephalitis Virus (VEEV), as well as nucleic acids which are used in the vectors, and methods of treatment using the vaccines.

The structural proteins of the alphaviruses are translated from a 26s RNA. The genes encoding these proteins are contained within a single open reading frame in the order:
capsid-E3-E2-6K-E1.

The capsid protein is also known as the "core" and both terms are used herein.

Each protein is either co- or post-translationally cleaved from the poly-protein precursor.

Many prophylactic and therapeutic vaccines rely on the use of recombinant viruses such as vaccinia virus, or adenovirus including replication competent and replication defective adenovirus, for effective delivery of the immunogens.

However, there are sometimes difficulties associated with the expression of alpha viruses in such vectors.

The applicants have found that deletion of a region of an alphavirus gene improves expression in certain vectors and allows expression in other vectors which could otherwise not be made. This is useful in vaccine production.

Thus according to the present invention there is provided a nucleic acid which encodes a polypeptide which produces a protective immune response against an alpha-virus in a mammal to which it is administered, said nucleic acid lacking a competant nuclear targeting signal from a capsid gene thereof.

The nucleic acid as described above may be expressed at enhanced levels, for example in an adenovirus.

As used herein, the term "polypeptide" encompasses short polypeptides as well as proteins. The expression "enhanced" means that the expression level of the polypeptide is increased as compared to that which would occur if an otherwise similar nucleic acid including the said portion of the nuclear targeting signal were present.

The nuclear targeting signal (NTS) of any particular alphavirus is either known or it can be determined by alignment with sequences which resemble known nuclear targeting signals in other alphaviruses. For instance, Jakob, Preparative Biochemistry (1995) 25: 99–117 shows the nuclear targeting signal in the Semliki forest virus. An example of a nuclear targeting sequence of VEEV is described below. These sequences are present in the gene encoding the core or capsid protein.

In general, the nuclear targeting signal will be located in a lysine rich area of the genome and will comprise a region which has at least 3 and generally 4 adjacent lysines such as described by Chelsky et al., 1989, Mol+Cell Biology, 9, p2487–2492. In the nucleic acids of the invention, the NTS is inactivated either by complete or partial deletion, or by mutation, for example to alter at least some of the lysine residues.

The nucleic acid of the invention may be a DNA or an RNA molecule, suitably a cDNA. Furthermore it suitably encodes a polypeptide which comprises at least one structural protein of said alpha-virus, and most preferably all of these. Thus, in a preferred embodiment, the recombinant nucleic acid of the invention encodes at least the capsid-E3-E2 proteings of the alpha-virus and more preferably the capsid-E3-E2-6K-E1 proteins of an alpha-virus, provided that the region which encodes the capsid protein lacks a competant nuclear targeting domain.

One alphavirus which has been found to benefit particularly from the present invention is a Venezulan Equine Encephalitis Virus (VEEV). This virus, is a mosquito-borne alphavirus which is an important cause of epidemic disease in humans and of epizootics in horses, donkeys and mules in certain parts of the world, in particular the South Americas.

The existing VEE vaccine, TC-83, was initially produced by attenuation of the Trinidad donkey strain (TRD) of VEE by sequential passage in guinea pig heart cell cultures. However, this vaccine is generally regarded as being inadequate for human vaccination. This is mainly due to the high incidence of side effects in vaccinees and the large proportion of vaccinees who fail to develop neutralising antibodies (Monath et al. 1992, Vaccine Research, 1, 55–68).

A vaccinia-based vaccine against VEE has been constructed (Kinney et al. J. Gen. Virol. 1988, 69, 3005–3013). In this recombinant, 26S RNA encoding structural genes of VEE were inserted into the NYCBH strain of vaccinia. The recombinant virus protected against sub-cutaneous challenge but had limited efficacy against aerosol challenge with VEE.

Attempts to express the full length sequence of this virus in adenovirus, a particularly useful virus for vaccine production, failed completely. However, certain deletion mutants could be successfully expressed. It has been found that the virus proteins will be expressed from a recombinant adenovirus which lacks at least some, and suitably all of nucleotides 7749–7887 within the VEEV genome.

All DNA sequence co-ordinants on the VEEV TC-83 strain followed those of the Trinidad Donkey virus strain (R. M. Kinney et al. Virology (1989) 170, 19–30). The cDNA of the 26s mRNA encoding the TC-83 structural region is that reported by Kinney et al (1988) supra, the content of which is incorporated herein by reference. The virulent Trinidad donkey strain of VEE and the attenuated strain TC-83 have both been cloned and sequenced and the amino acid and nucleotide numbering system used in this reference will be used hereinafter. This work revealed that there are seven amino acid changes between TRD and TC-83. The majority (five) of these changes occur within the gene encoding the glycoprotein E2. The applicants have found a further three changes over and above those described by Kinney as detailed below.

The deletion or omission of a nuclear targeting domain has also been found to improve the expression of other VEEV encoded proteins in other vectors such as plasmids.

Deletion of corresponding regions in other alphaviruses should produce similar enhancements in expression.

The recombinant nucleic acids of the invention may be prepared by any of the well known techniques used in recombinant DNA technology. They may be prepared ab initio using the available chemical methods, for example the automated chemical synthesisers. Alternatively, they may be prepared from wild-type alpha viruses, using known recombinant DNA techniques to generate deletion mutants.

Thus in a further aspect the invention provides a deletion mutant of an alpha-virus, which mutant lacks a nuclear targeting domain, such as a region corresponding to nucleotides 7749–7887 of VEEV. Corresponding regions in other alphaviruses could be readily be determined by comparing sequences and determining analogous regions as is understood in the art. Such comparisons can be made by computer programs.

Confirmation of the nature of the nuclear targeting domain can be confirmed, for example using labelled fragments which may or may not include the purported nuclear targeting domain, and examining where the label appears when the fragments are located in cells transfected with the fragments. The labels may be radiolabels or fluorescent labels as are well known in the art.

Preferably the deletion mutant of the invention is a deletion mutant of VEEV.

A further aspect of the invention provides a recombinant nucleic acid which encodes a deletion mutant of an alpha-virus as described above.

Nucleic acids of the invention are suitably incorporated into vectors, in particular virus vectors like adenovirus (which may be either replication competent or replication defective), vaccinia virus, or in other expression plasmids where they are under the control of a suitable promoter as understood in the art. Preferably the nucleic acids of the invention is incorporated into an adenovirus and most preferably a replication defective adenovirus.

These viruses or plasmids can form vaccines. For this purpose, they will suitably be combined with a pharmaceutically acceptable carrier. Virus vectors are preferably combined with a liquid carrier in an injectable formulation. Plasmid vectors may also be made into an injectable formulation or they may alternatively be bound onto a solid carrier such as a gold bead, which are suitable for administration by means of a gene gun, to the skin of a patient.

In yet a further aspect, the invention provides a method of producing a protective immune response to an alpha-virus, said method comprising administering to a mammal a vaccine as described above. The protective immune response may be used both in prophylaxis and in therapy. Suitable doses will be determined by clinicians taking into account the nature of the patient, the nature of the alphavirus and in the case of therapeutic treatment, as well as the precise nature and form of the vaccine. However in general, when using a virus vector, dosages of the vector will be of at least $10^4$ pfu. For instance, in the case of vaccinia vectors or replication competent adenovirus, dosages are suitably in the range of from $10^4$–$10^{12}$ pfu (pfu=particle forming units). Replication defective adenovirus may have to be administered at higher dosages.

BRIEF DESCRIPTION OF THE DRAWINGS

The invention will now be particularly described by way of example with reference to the accompanying diagrammatic drawings in which:

FIG. 2 shows the sequences of various adapters and primers (SEQ ID NOS:1–18) used in the constructs of the Examples.

In the following Examples, the abbreviations used are as follows:

| | |
|---|---|
| VEEV | Venezuelan Equine Encephalitis Virus |
| TRD | Trinidad Donkey Virus Strain |
| C | Core |
| E1 | Structural protein 1 |
| E2 | Structural protein 2 |
| E3 | Structural protein 3 |
| 6K | Structural protein 6K |
| CMV | Cytomegalovirus |
| IEP | Immediate Early Promoter |
| Term | Terminator signal |
| cDNA | Complementary DNA |
| RAd | Recombinant E1a- Adenovirus |
| NCR | Non-Coding Region |
| ATG | Start Codon |
| MCS | Multiple Cloning Site |
| NTS | Nuclear Targeting Signal |
| RBS | Ribosome Binding Site |
| nt | Nucleotide |
| nts | Nucleotides |
| PCR | Polymerase Chain Reaction |
| Δ | Minus |

The cDNA of the 26s sub-genomic RNA encoding the TC-83 structural region is that used in the work described below and was provided on the plasmid pTC-5a as reported by Kinney et al. (1988). J.G.V. 69: 3005–3114. All VEEV TC-83 cDNA sequence co-ordinates described below followed those Kinney and co-workers (Kinney et al. (1989). Virology 170: 19–33) for the VEEV strain Trinidad donkey (TRD). Nucleotide sequence analysis of the TC-83 VEEV cDNA identified three differences in addition to those described (Kinney et al. (1989). Virology 170: 19–33) within the open reading frames of TC-83 and TRD. These changes are; i) within the 6K gene of TC-83 an addition codon GCG is located between nucleotides (nts) 9989 and 9990, ii) within the E1 gene of TC-83 nt 10353 is T, and ii) in E1 gene of TC-83 nt 18897 is G.

EXAMPLE 1

Preparation of Deletion Mutants

Figure 3:
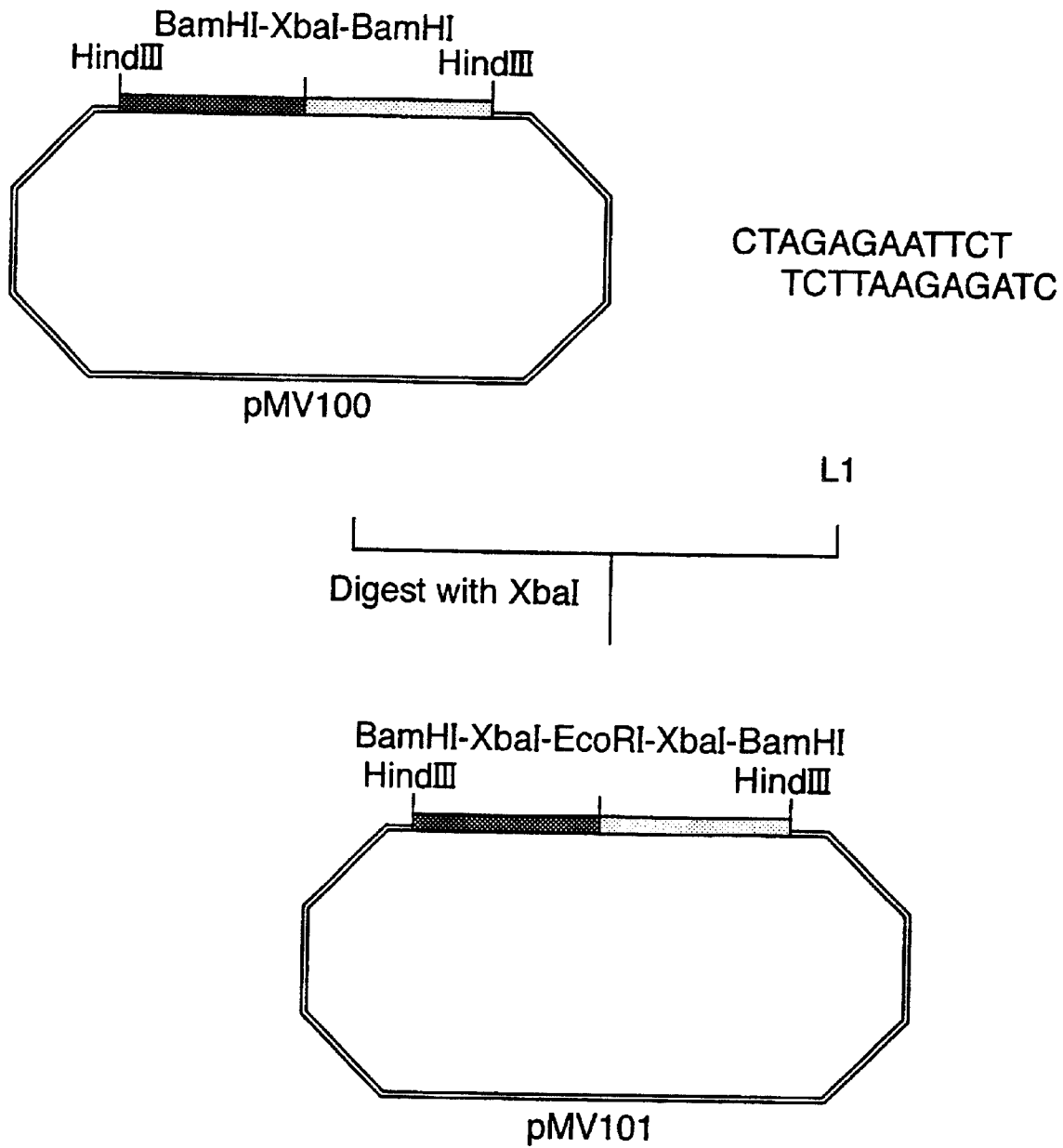
FIGS. 3–28 are the cloning diagrams referred to in the Examples: L1 (SEQ ID NOS:1–2) is shown in FIG. 3, L4A (SEQ ID NOS:3–4) is shown in FIG. 5, L7L8 (SEQ ID NOS:5–6) is shown in FIG. 7, L5L6 (SEQ ID NOS:7–8) is shown in FIG. 8, L10L13 (SEQ ID NOS:9–10) is shown in FIG. 11, L28L29 (SEQ ID NOS:11–12) is shown in FIG. 19, and L30L31 (SEQ ID NOS:13–14) is shown in FIG. 22.

All constructs were cloned into the expression cassette contained within pMV100 or pEVV101. pMV100 has been described previously (Wilkinson and Akrigg. (1992) N.A.R. 20: 2233–2239, Jacobs et al. (1992) J. Virol 66: 2086–2095). The insertion at the XbaI site in pMV100 of the palindromic adapter L1 (FIG. 2a) which encodes an EcoRI site on an XbaI fragment generated pEVV101 (FIG. 3). Thus this modification adds an EcoRI site in between the CMV immediate early promoter (IEP) and terminator signal (Term) allowing cDNA to be cloned into the expression cassette (or to be excised from it) on a BamHI, XbaI or EcoRI restriction fragment.

Figure 4:
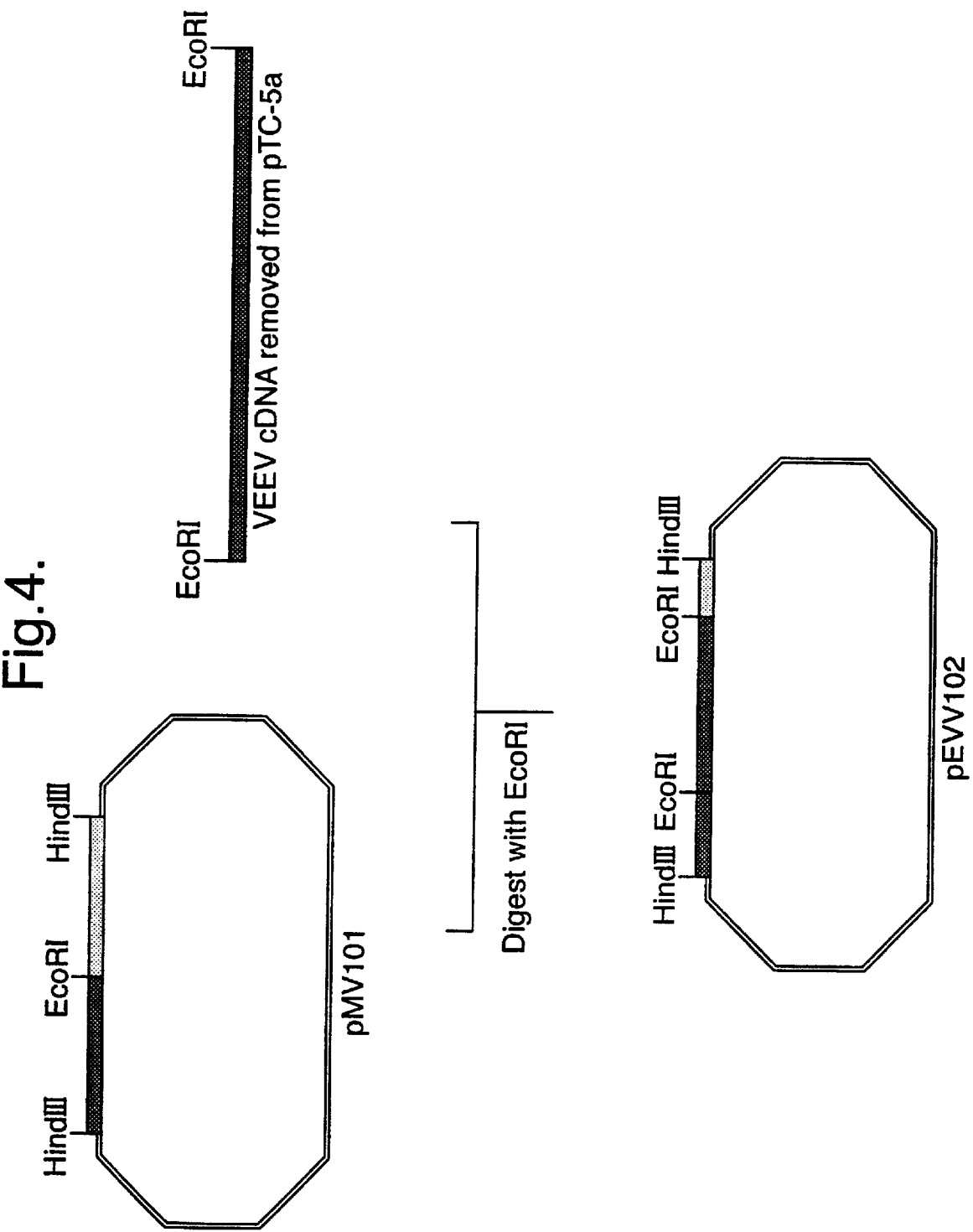

Recombinant E1a-adenovirus 5 (Rad) was generated using materials, including the shuttle vector pMV60, and methods described elsewhere(Wilkinson and Akrigg. (1992) N.A.R. 20: 2233–2239, Jacobs et al. (1992) J. Virol 66: 2086–2095). The VEEV cDNA from pTC-5a was cloned into pEVV101 on an EcoRI fragment generating pEVV102 (FIG. 4). The expression cassette containing the VEEV cDNA was subcloned from a pEVV102 into pMV60 on a HindIII fragment generating pEVV105. RAd could not be generated with pEVV105 or other plasmids similarly constructed. RAd was made, however, when the VEEV cDNA was cloned in the wrong orientation under the control of the promoter.

Figure 5:
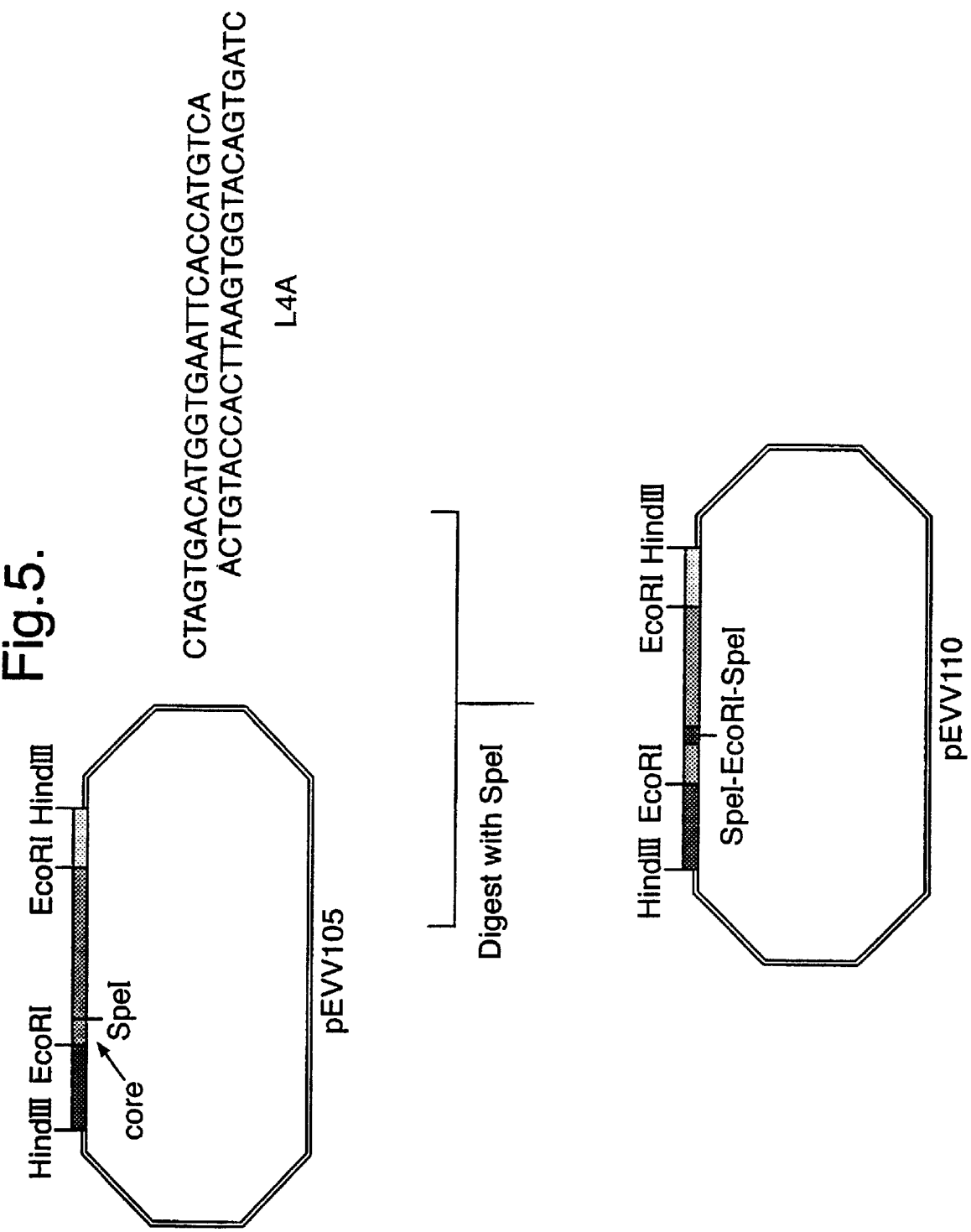
Figure 6:
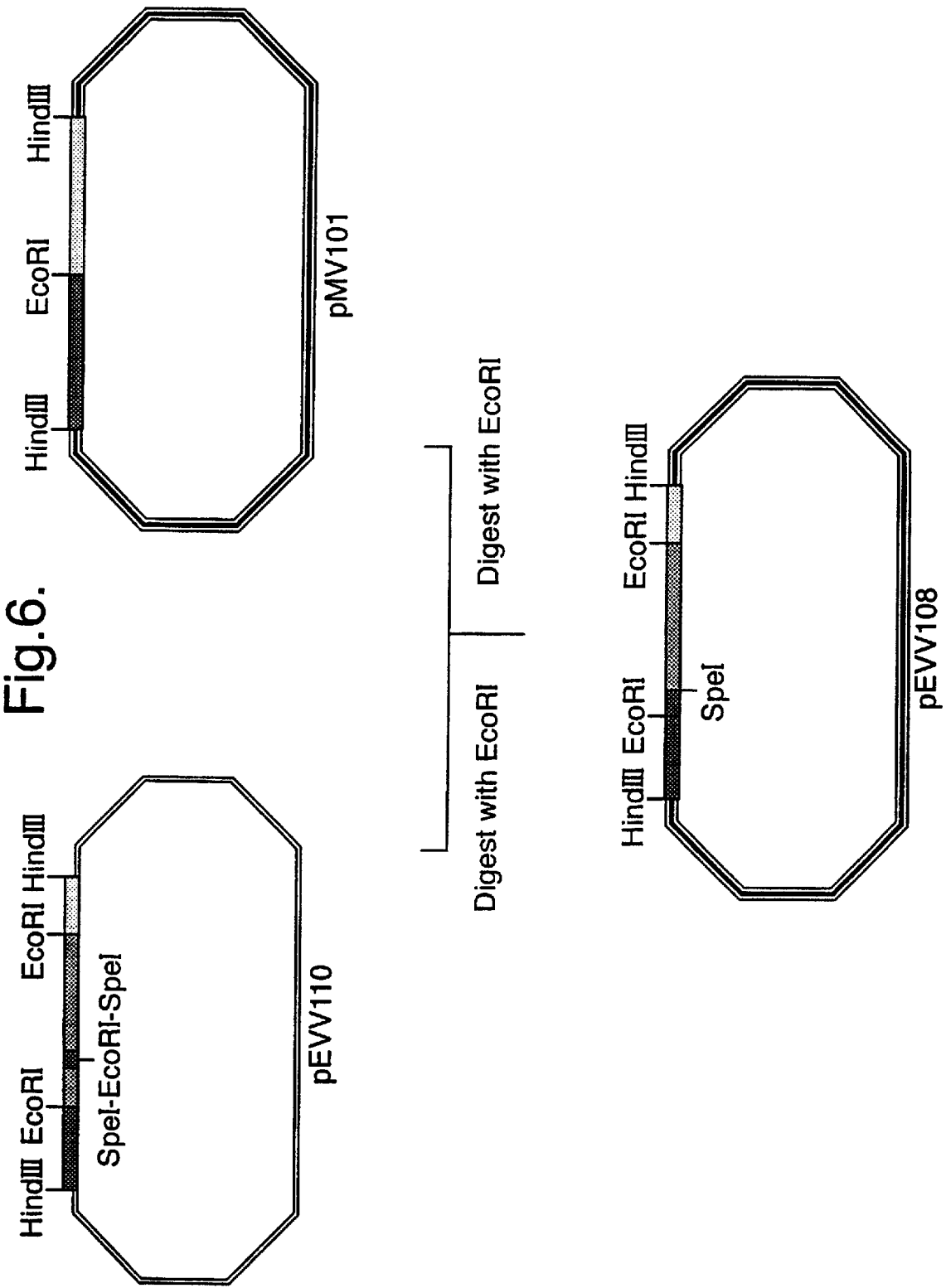

The truncated 5' non-coding region (NCR) and core gene (5'-C) were deleted from the TC-83 VEEV cDNA to investigate whether RAd could be made containing the E3-E2-6K-E1 and the truncated 3' NCR (E3-E2-6K-E1-3'). pEVV105 was digested with SpeI cutting the VEEV cDNA immediately downstream of nt 8389, three nucleotides into the 5' of the E3 gene. The three deleted nucleotides were restored by the insertion of the palindromic adapter L4A (FIG. 2b) at the SpeI site generating pEVV110 (FIG. 5). L4A also encoded a start codon immediately upstream of the three 5' nts of the E3 gene, which is preceded by a Kozak consensus sequence ACC (Kozak. (1984). Nature 308: 241–246, Kozak. (1986). Cell 44: 283–292, Kozak. (1987). J. Mol. Biol. 196: 947–950) and an EcoRI site. Using the EcoRI site in L4A and that at the 3' of the VEEV cDNA, the cDNA VEEV construct E3-E2-6K-E1-3' was removed from pEVV110 and cloned into pEVV101 generating pEVV108 (FIG. 6). The expression cassette containing the VEEV cDNA was subcloned from pEVV108 to pMV60 on a HindIII fragment generating pEVV109. RAd was generated using pEVV109.

Figure 7:
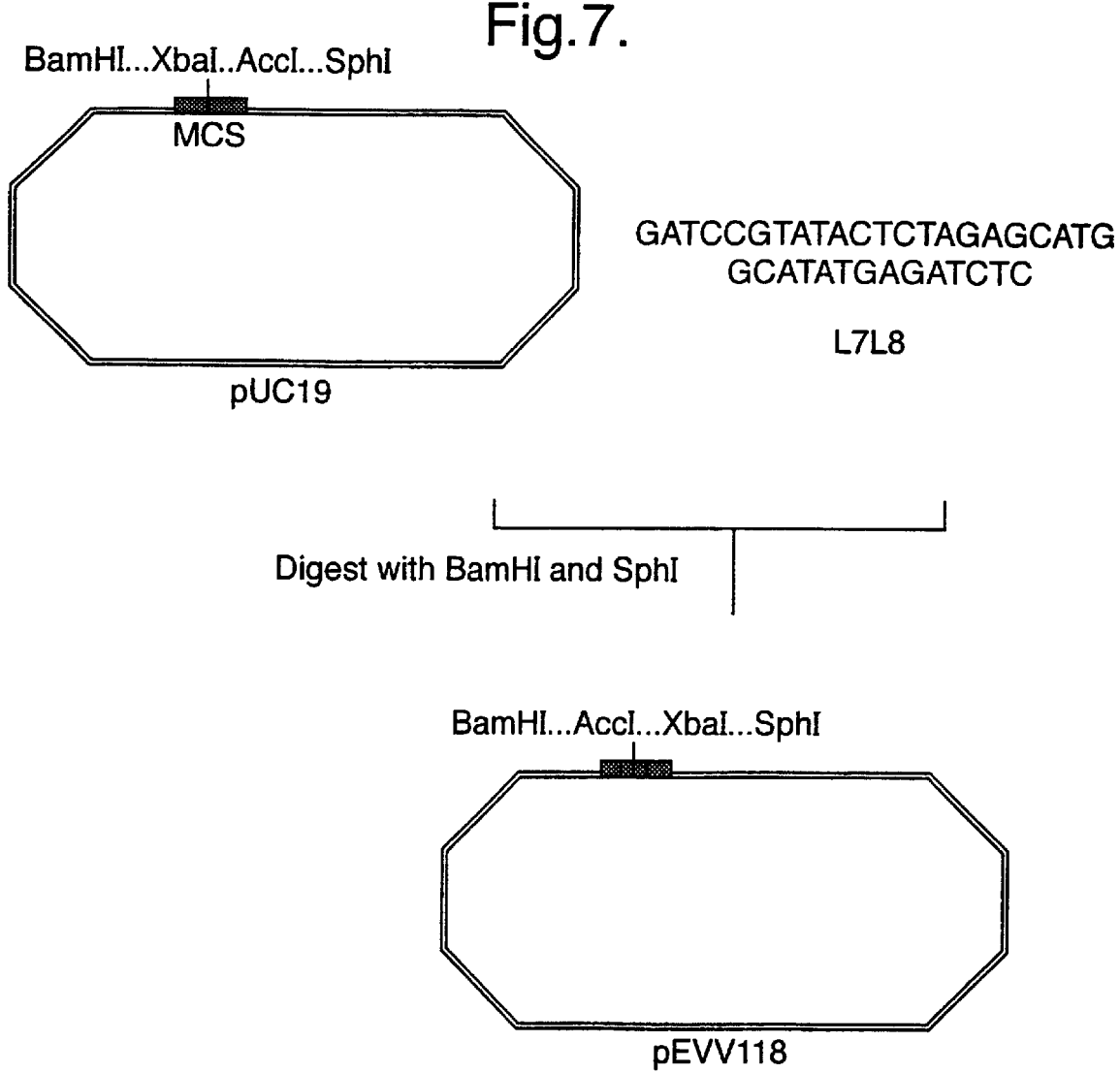
Figure 8:
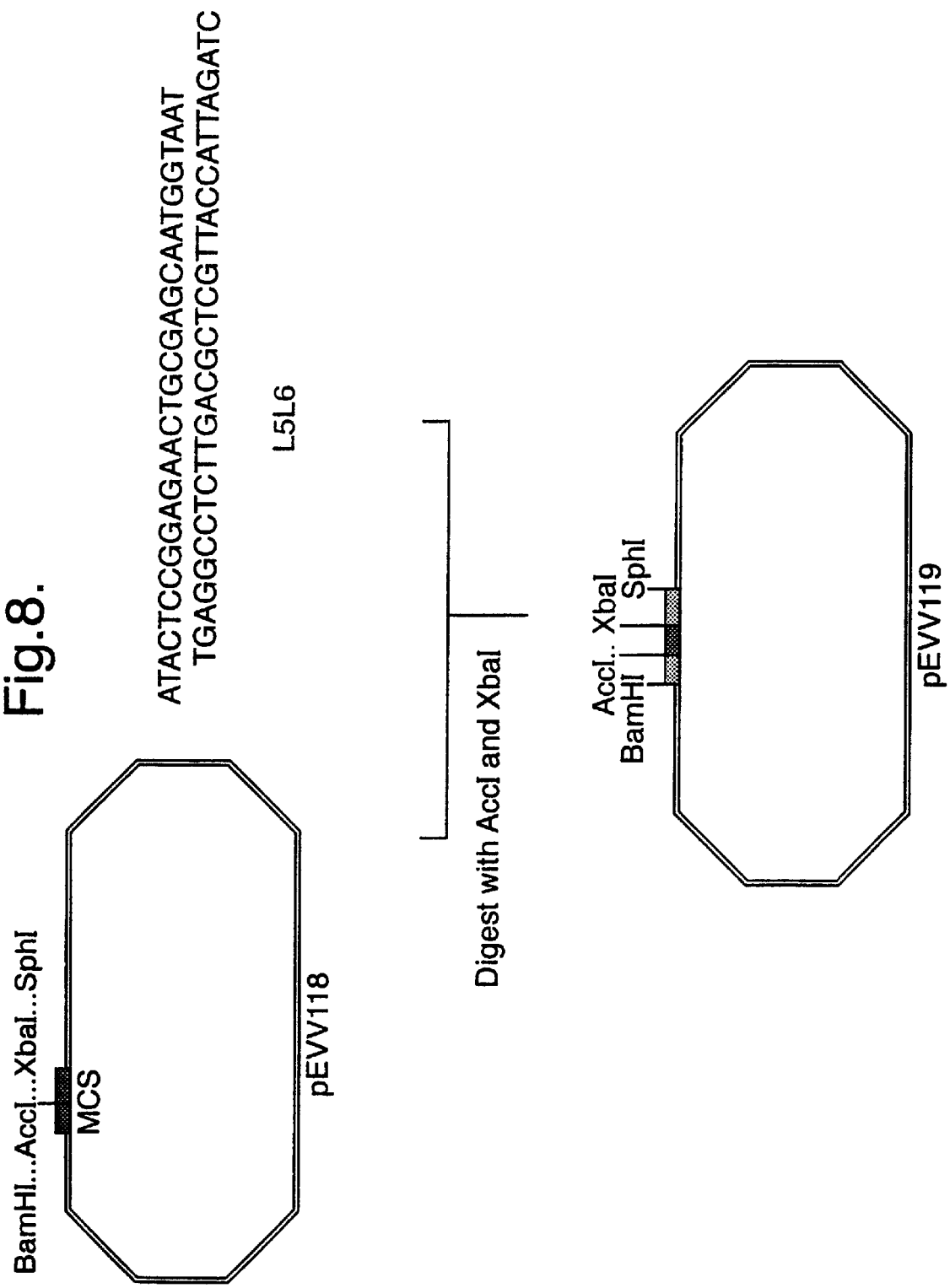
Figure 9:
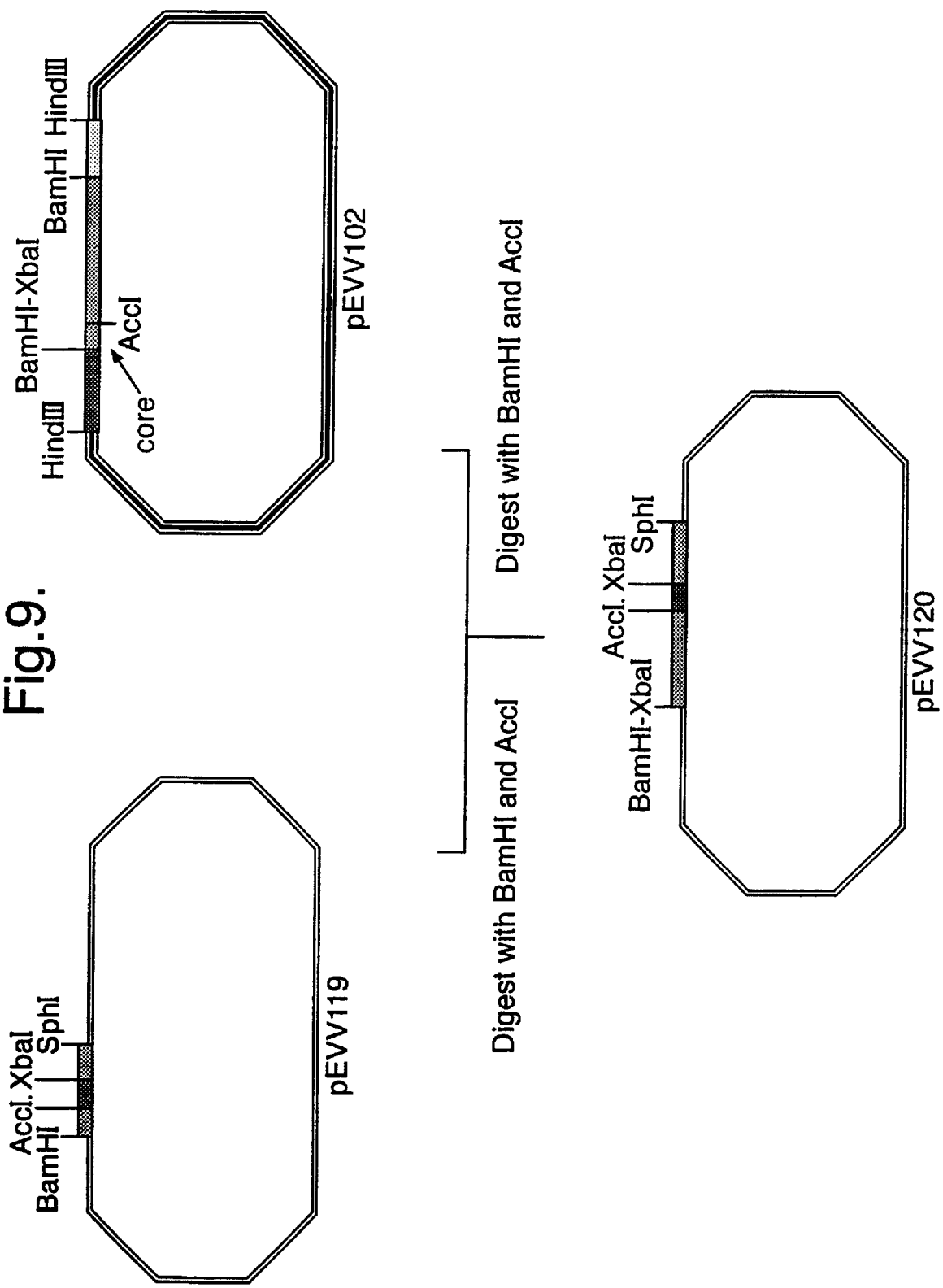
Figure 10:
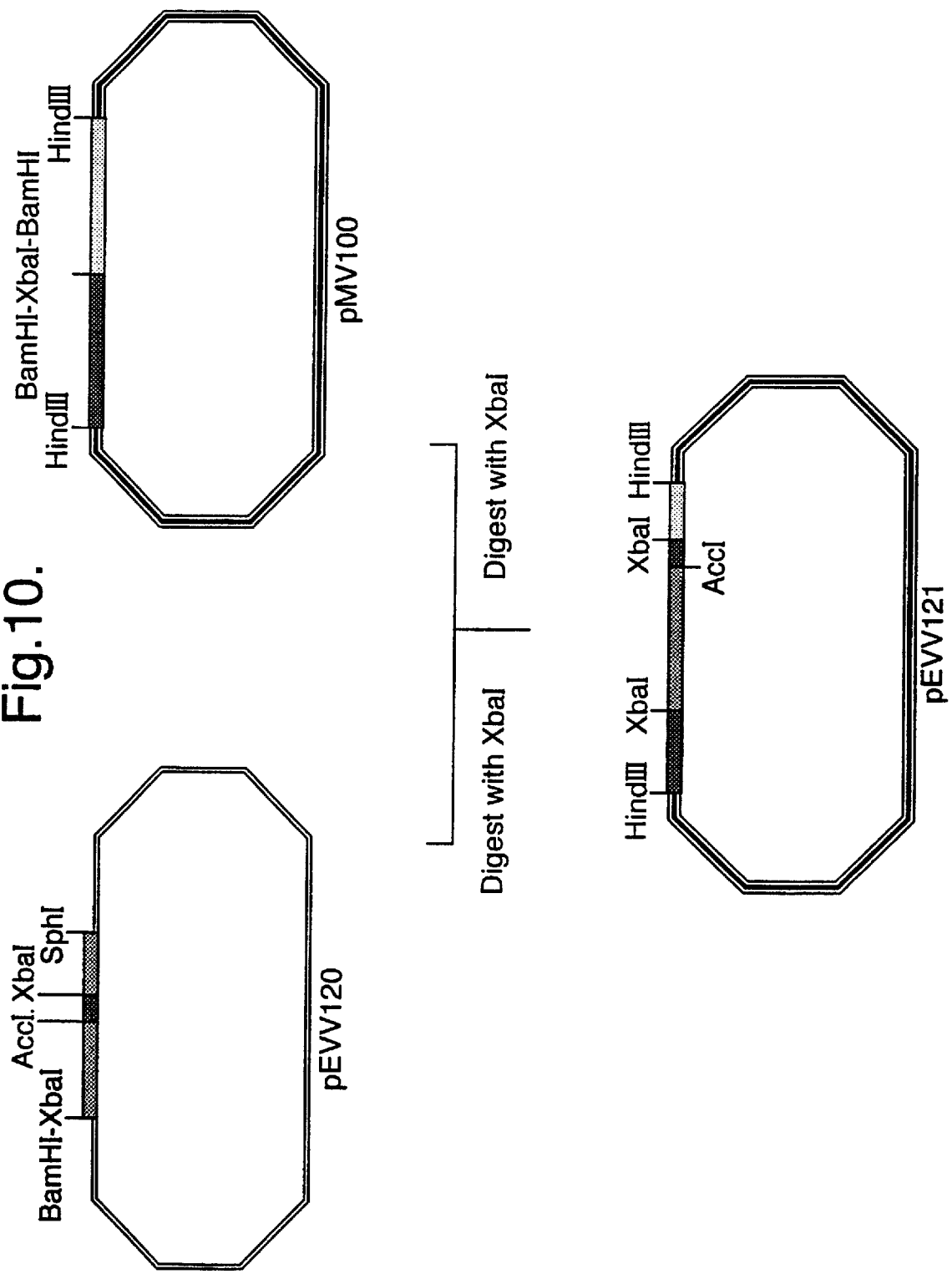

An attempt was made to generate RAd expressing the truncated 5' NCR and core (5'-C). To clone 5'-C, the plasmid pUC19 (provided by Boehringer Mannheim UK) was modified by reversing the order of the XbaI and AccI sites within the multiple cloning site (MCS). A BamHI and SphI adapter encoding an AccI and XbaI site (L7L8, FIG. 2c) was inserted into the MCS of pUC19 to generate pEVV118 (FIG. 7). The adapter L5L6 (FIG. 2d) provided the 3' 26 nucleotides of core gene from the AccI site (nt 8361) to the 3' of core at nt 8386 and an appropriate stop codon on an AccI/XbaI fragment and was cloned into pEVV118 generating pEVV119 (FIG. 8). The 5' NCR and remaining 5' of the core gene, up to and including nt8360, was removed from pEVV102 on a BamHI-AccI fragment and cloned into pEVV119 completing the constructing of 5'-C and generating pEVV120 (FIG. 9). The 5'-C fragment was removed from pEVV120 on an XbaI fragment and cloned into pMV100 generating pEVV121 (FIG. 10). The expression cassette containing 5'-C was subcloned from pEVV121 into pMV60 on a HindIII fragment generating pEVV123. RAd could not be generated using pEVV123.

Figure 11:
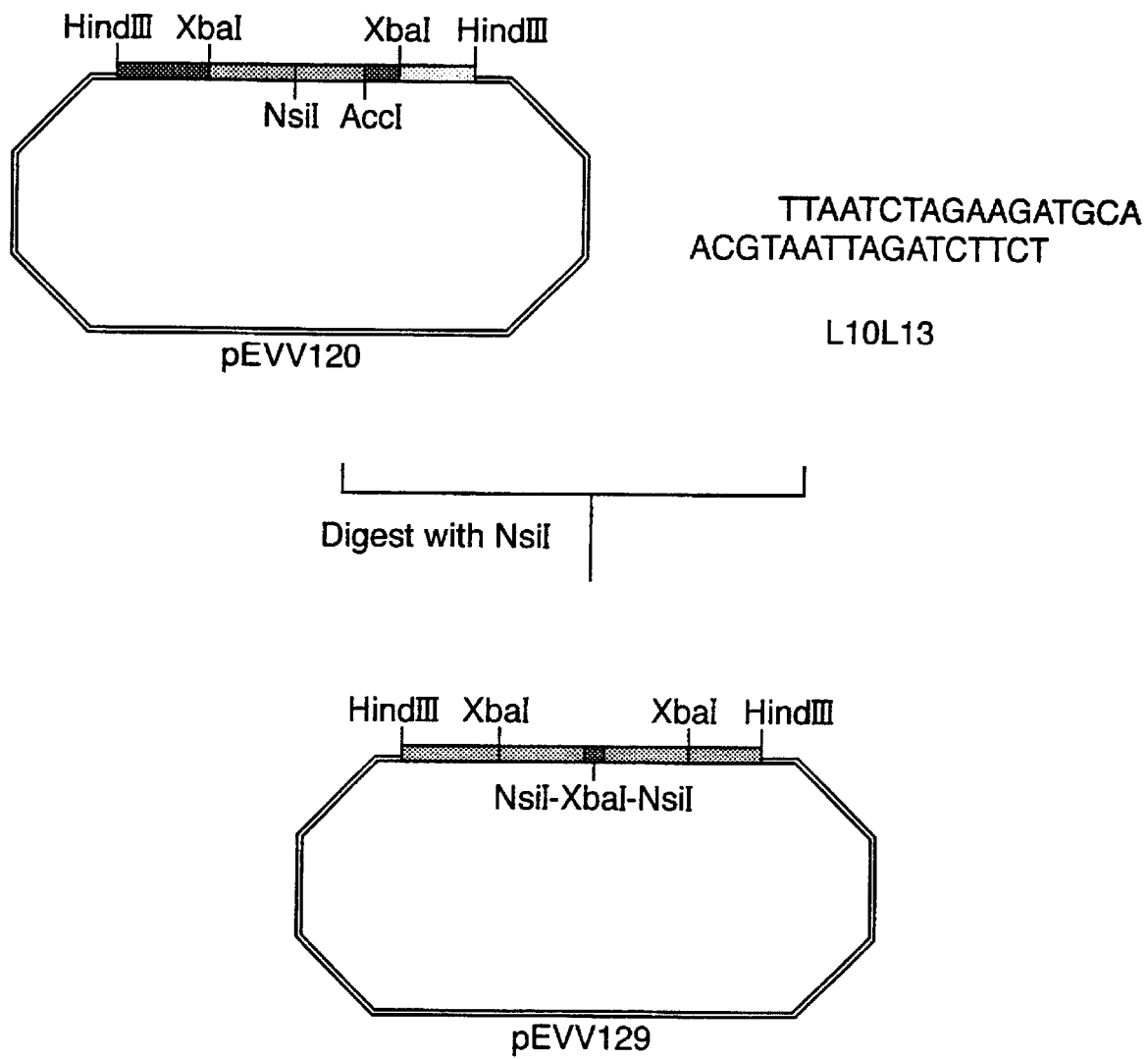
Figure 12:
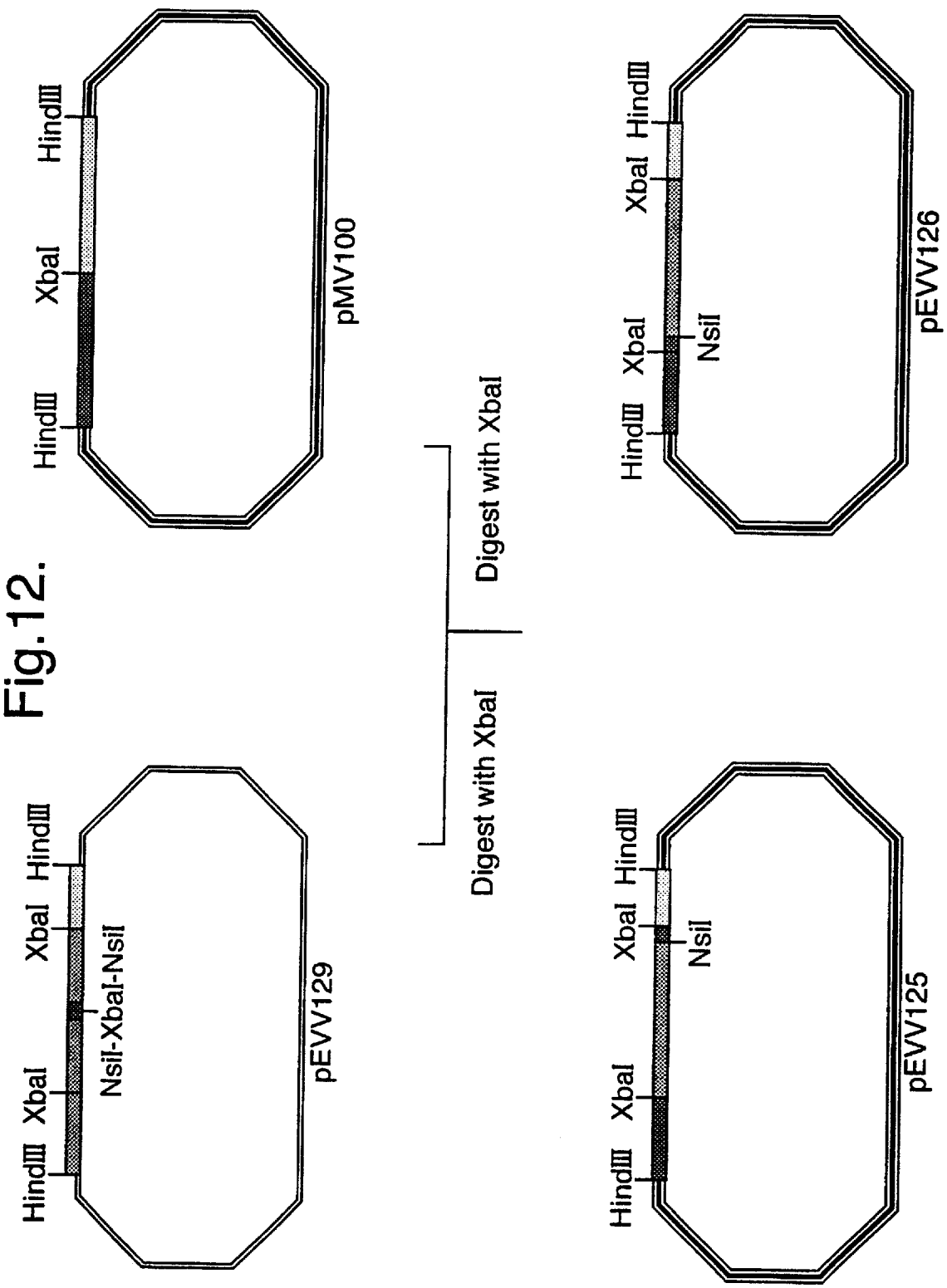

In an attempt to identify the domain responsible for the failure to generate RAd containing core, the VEEV core gene was cloned in two halves. The adapter L10L13 (FIG. 2e) was inserted at the NsiI site in core between nucleotides 8016 and 8017. This placed an in frame stop codon downstream of the NsiI site followed by an XbaI site, an in frame start codon and a second NsiI site. The resultant plasmid (pEVV129, FIG. 11) was digested with XbaI generating two fragments containing C sequence. One containing the 5' NCR and the 5' of core up to and including nt 8016 which immediately precedes an inframe stop codon. The second containing the 3' of the core gene from nt 8017 which is immediately preceded by an in frame start codon, up to and including the stop codon inserted in the construction of 5'-C (i e. pEVV121). Each fragment was cloned into pMV100 on an XbaI fragment generating pEVV125 (FIG. 12) which encodes the 5' of core and pEVV126 (FIG. 12) which encodes the 3' of core. The expression cassette were subcloned from pEVV125 and pEVV126 into pMV60 on a HindIII fragment generating pEVV127 and pEVV128 respectively. RAd could not be generated using pEVV127 but was generated from the pEVV128.

Three domains within the 5' of core encoded by pEVV125 that might be responsible for the failure to generated RAd virus containing core were identified. These domains are i) the 17 nts upstream of the start codon at nt7562 which form the truncated 5' NCR; ii) the putative ribosome binding site (RBS) between nt 7886–7930 identified by sequence alignment with the alphaviruse Sindbis (Wengler et al. (1992). Virol; 191: 880–888, Geigenmuller-Gnirke et al. (1993). J Virol 67: 1620–1626, Owen and Kuhn. (1996). J. Virol 70: 2757–2763); iii) a putative nuclear targeting signal (NTS) between nt 7751–7885 identified by sequence alignment with the alphavirus Semliki forest virus (Jakob. (1995). Preparative Biochemistry 25: 99–117).

Figure 13:
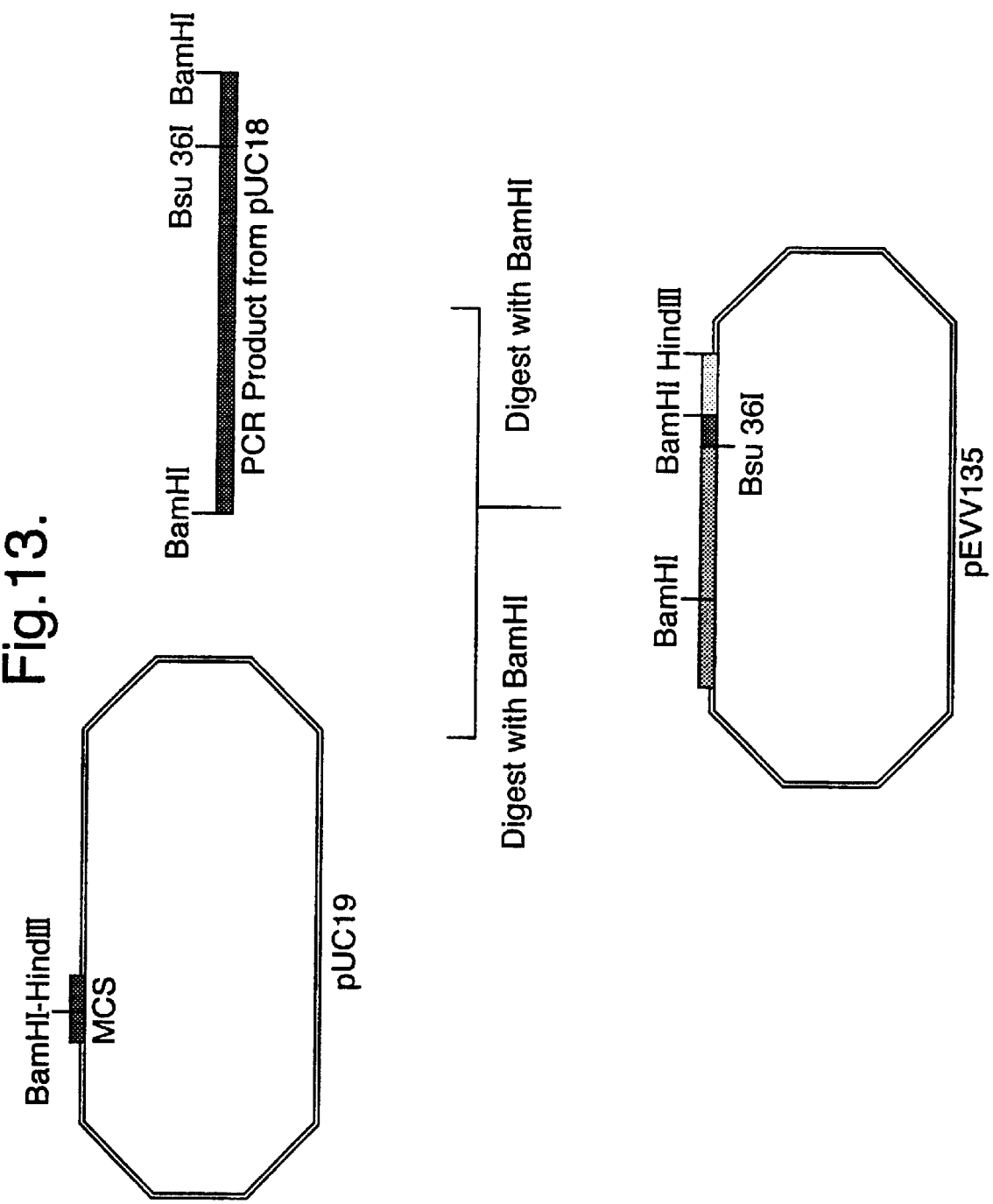
Figure 14:
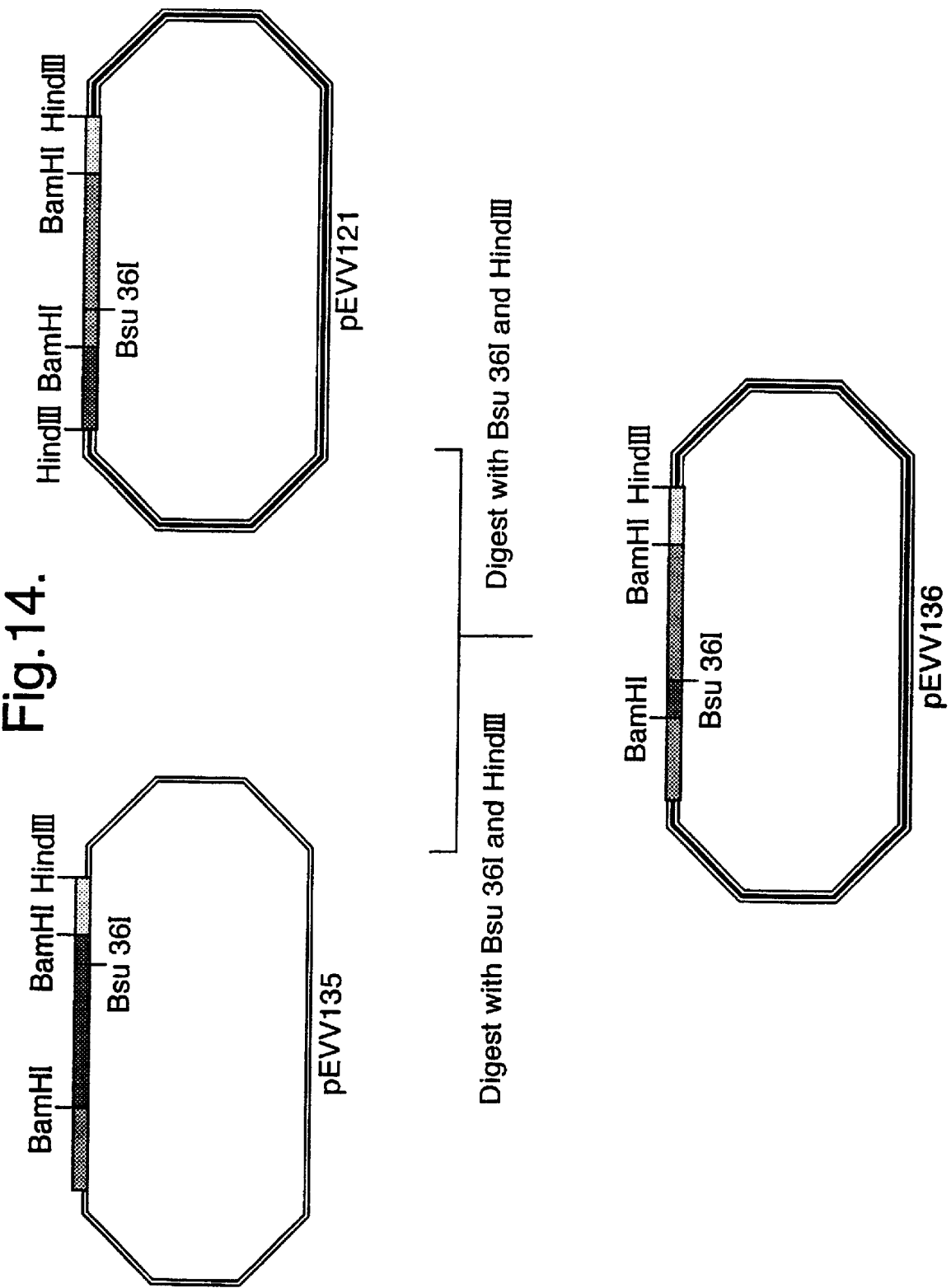
Figure 15:
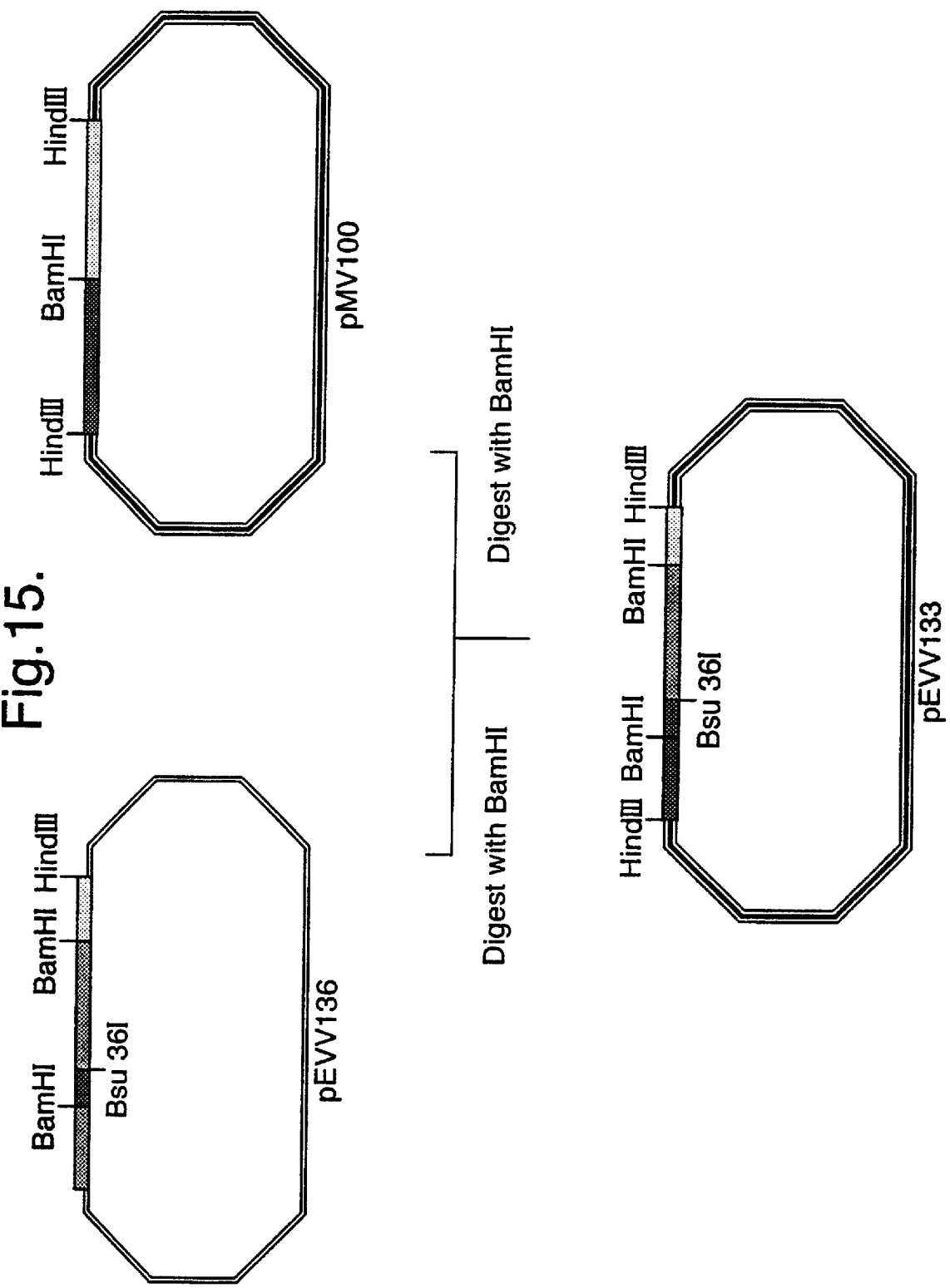

To remove the 5' NCR from core, a PCR fragment was generated with primer P2 (FIG. 2h) and P3 (FIG. 2i) using pEVV123 as the template. From 5' to 3', P2 contains a GC rich tail, BamHI site, and the 17 nts homologous to the positive strand of the 5' of the core gene from the start codon at nt 7562. From 5' to 3', P3 contains a GC rich tail and BamHI site followed by 14 nucleotides complementary the positive strand the core gene between nt 7726–7739 including a Bsu 36I site located between nt 7733–7739. The resultant PCR product therefore contained BamHI sites which flanked sequence containing the 5' of core from the start codon at nt 7562 up to and including the internal Bsu 36I site (nt 7739). This PCR product was digested with BamHI and cloned into pUC18 (provided by Boehringer Mannheim UK). The BamHI fragment was then subcloned into pUC19 generating pEVV135 (FIG. 13). Reconstruction of core gene was completed by inserting the remaining 3' of core from the Bsu 36I site (nt 7735) up to and including the stop codon following nt8386 from pEVV121 on a Bsu 36I-HindIII fragment into pEVV135 generating pEVV136 (FIG. 14). The core gene was removed on a BamHI fragment from pEVV136 and cloned into pMV100 generating pEVV133 (FIG. 15). The expression cassette containing the Core was subcloned from pEVV133 into pMV60 on a HindIII fragment generating pEVV134. RAd could not be generated using pEVV134.

Figure 16:
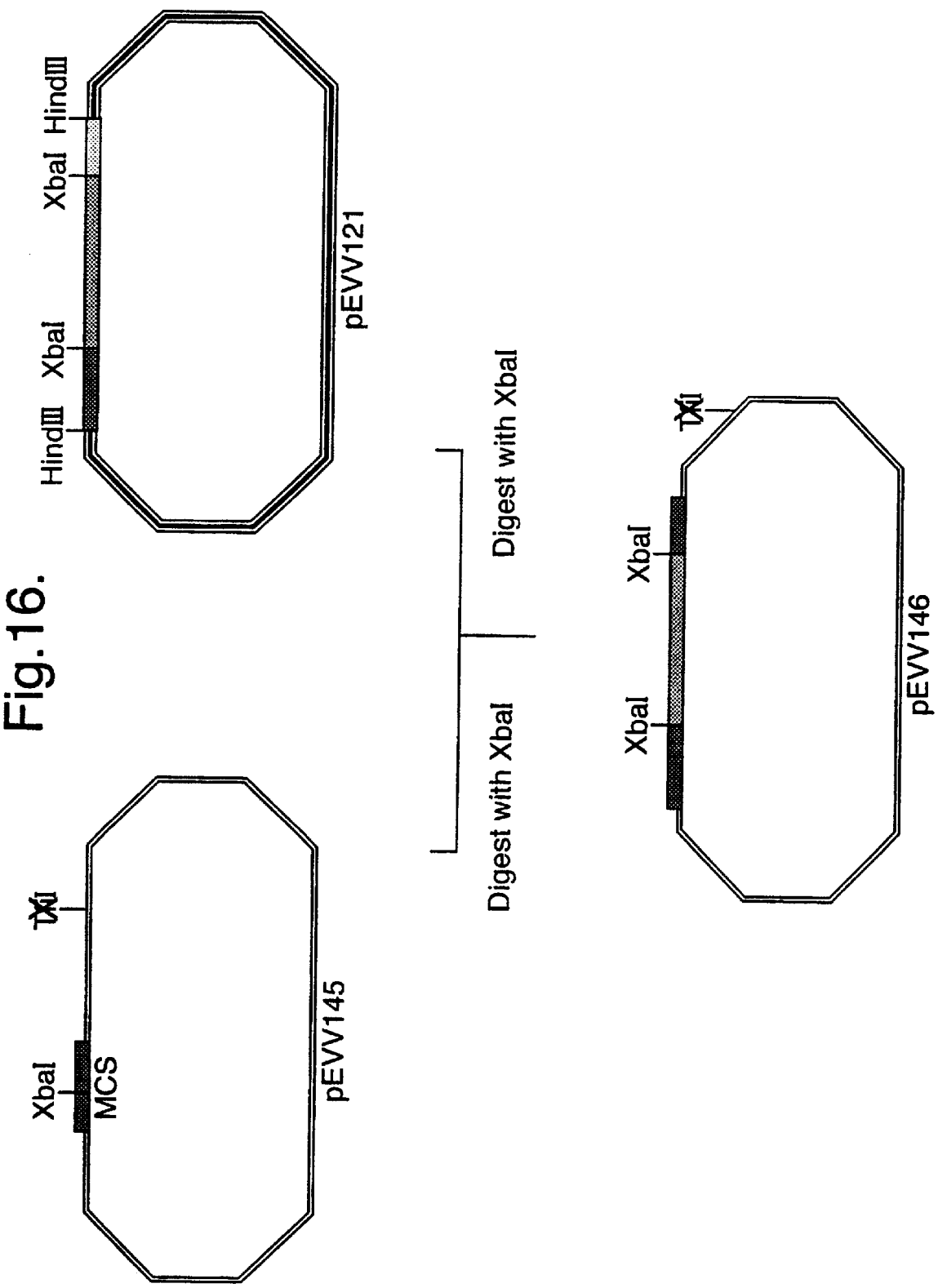

To delete the RBS from core, a TfiI site within core was used which necessitated the removal of the TfiI sites at nt641 and 781 in pUC19. pUC19 was digested with TfiI and the sticky ends generated were modified with Klenow before the plasmid was re-ligated generating pEVV145. Core was cloned into the MCS of pEVV145 on an XbaI fragment from pEVV121 generating pEVV146 (FIG. 16). To delete either the NTS or RBS from core it was necessary to remove both signals on a Bsu 36I-TfiI fragment (nts 7735–7928) and then restore either the NTS or RBS separately. This was achieved by digesting pEVV146 with Bsu 36I and TfiI and replacing the RBS-NTS fragment with either a Bsu 36I-TfiI PCR fragment encoding the NTS or a Bsu 36I-TfiI adapter encoding the RBS.

Figure 17:
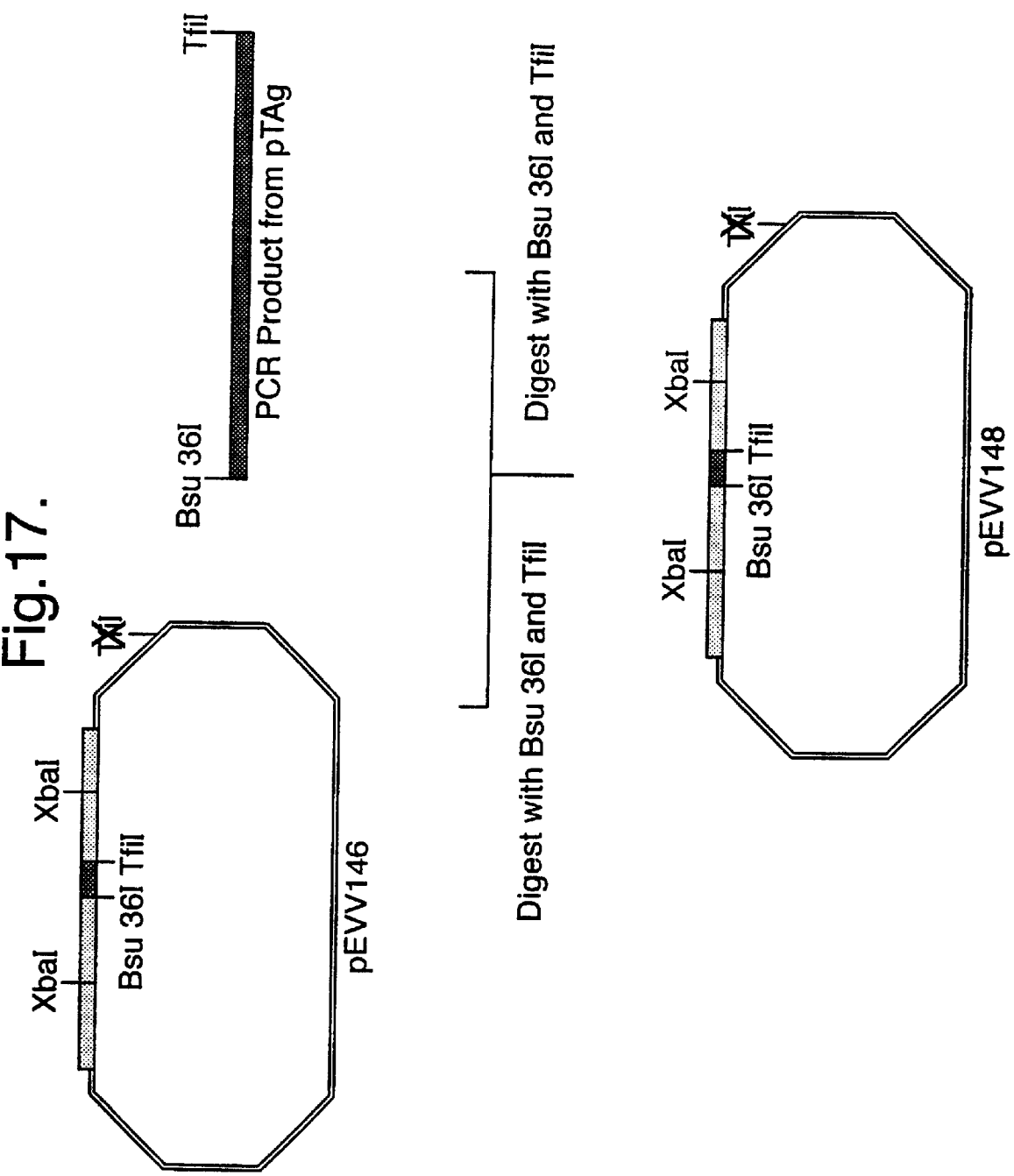
Figure 18:
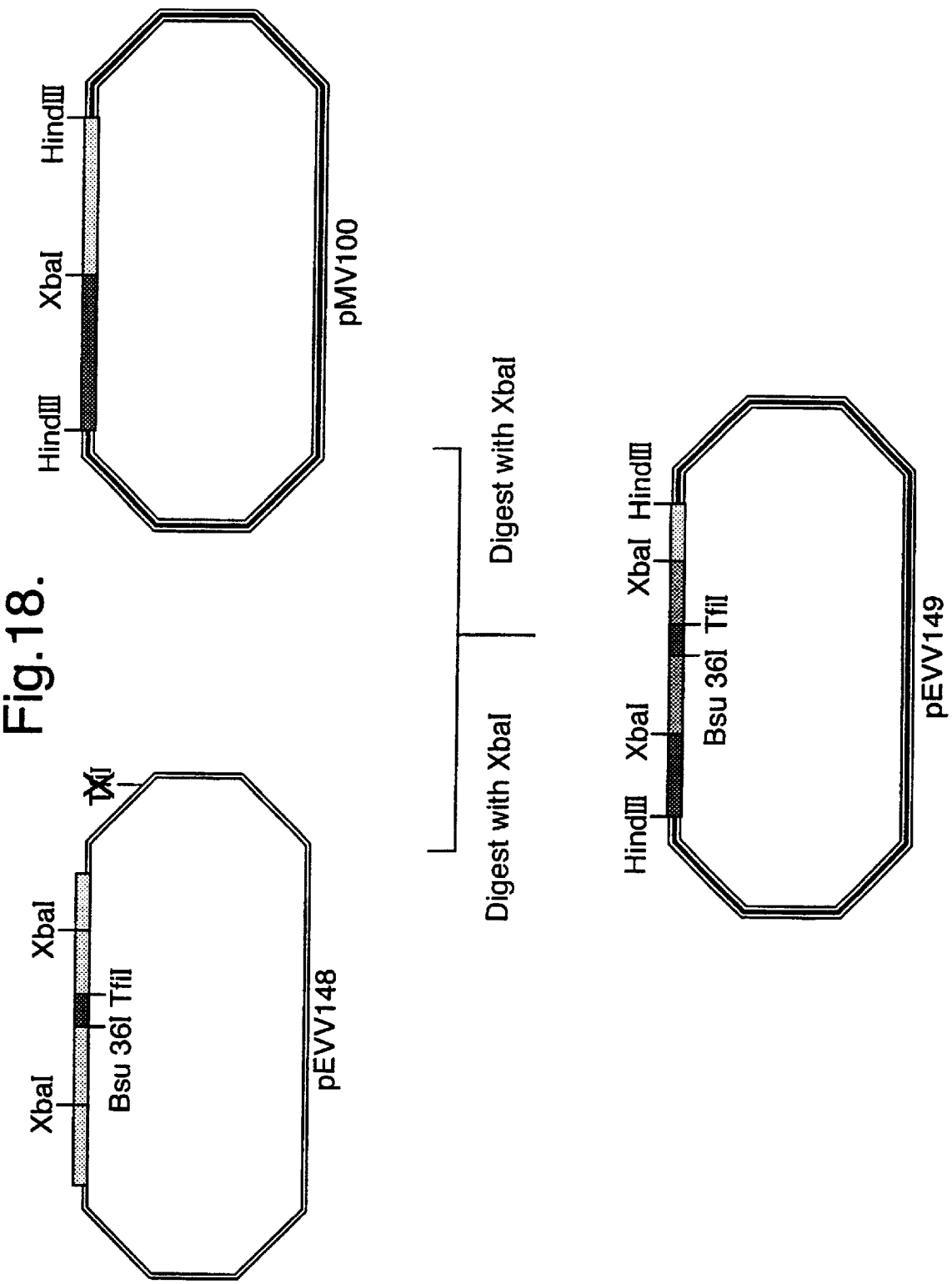

A Bsu 36I-TfiI PCR fragment containing the NTS was generated using primers L20 and L21 (FIGS. 2j and 2k). L20 is homologous to the positive strand of core gene and encodes a Bsu 36I site followed by the 10 nt from 7735 to 7749, L21 encoded 25 nts complementary to the positive strand of the core gene between nts 7872–7897 followed by a TfiI site. The PCR fragment was cloned into pTAg (R & D Systems Europe LTD) using the nontemplated-dependent single A added to the 3' ends of the PCR product. The Bsu 36I-TfiI fragment containing the NTS was then excised from pTAg and cloned into pEVV146 replacing the Bsu 36I-TfiI fragment containing the NTS and RBS and generating core minus (ΔRBS (CΔRBS)(pEVV148 (FIG. 17)). CΔRBS was removed from pEVV148 and cloned into pMV100 on XbaI fragment generating pEVV149 (FIG. 18). The expression cassette containing CoreΔRBS was subcdoned from pEVV149 into pMV60 on a Hindlil fragment generating pEVV150. RAd could not be generated using pEVV150.

Figure 1:
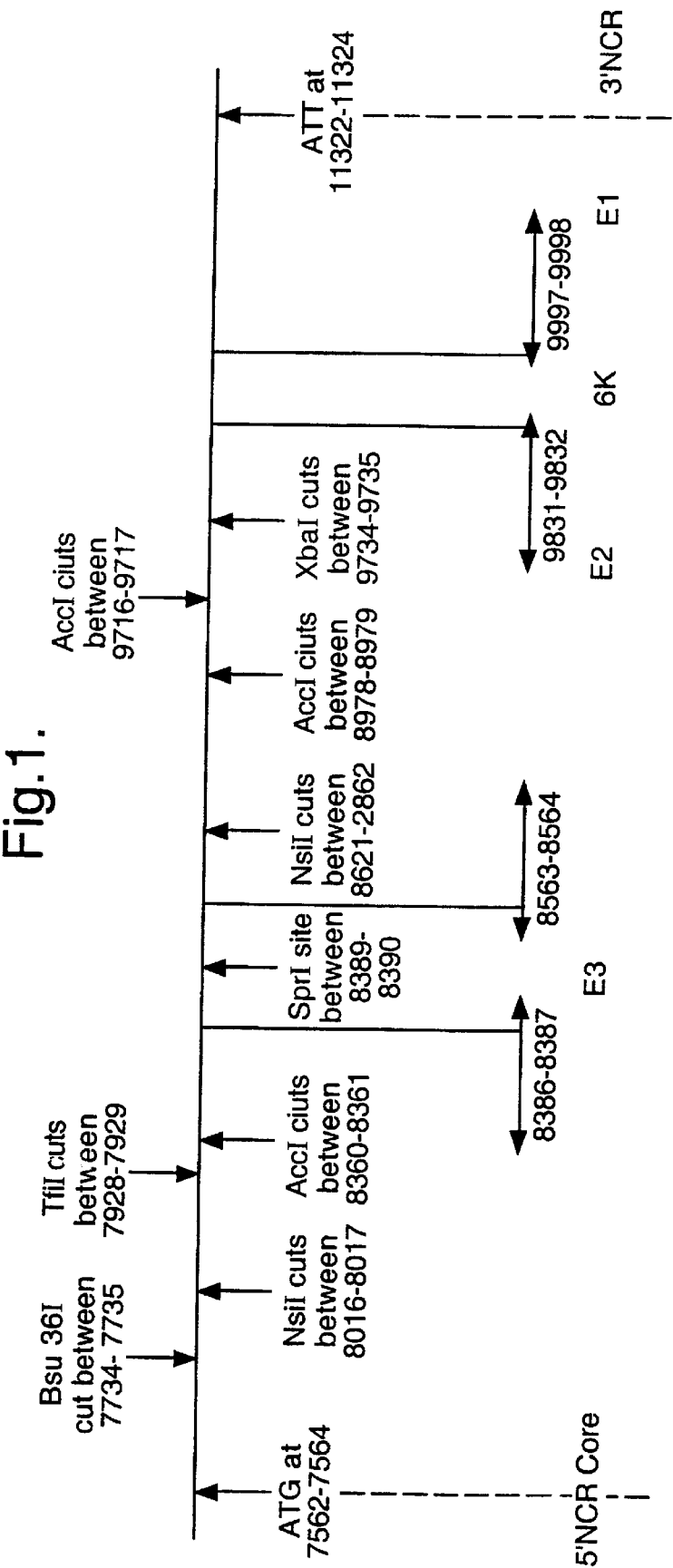
FIG. 1 is a diagrammatic map (not to scale and not inclusive) showing the structure of VEEV cDNA including restriction sites and the coding regions for the various proteins.

Bsu 36I-TfiI PCR fragment containing the NTS was generated using primers L20 and L21 (FIGS. 1j and 1k). L20 is homologous to the positive strand of core gene and encodes a Bsu 36I site followed by the 10 nt from 7735 to 7749, L21 encoded 25 nts complementary to the positive strand of the core gene between nts7872–7897 followed by a TfiI site. The PCR fragment was cloned into pTAg (R & D Systems Europe LTD) using the nontemplated-dependent single A added to the 3' ends of the PCR product. The Bsu 36I-TfiI fragment containing the NTS was then excised from pTAg and cloned into pEVV146 replacing the Bsu 36I-TfiI fragment containing the NTS and RBS and generating core minus (ΔRBS (CΔRBS) (PEVV148 (FIG. 17)). CΔRBS was removed from pEVV148 and cloned into pMV100 on XbaI fragment generating pEVV149 (FIG. 18). The expression cassette containing Core ΔRBS was subcloned from pEVV149 into pMV60 on a HindIII fragment generating pEVV150. RAd could not be generated using pEVV150.

Figure 19:
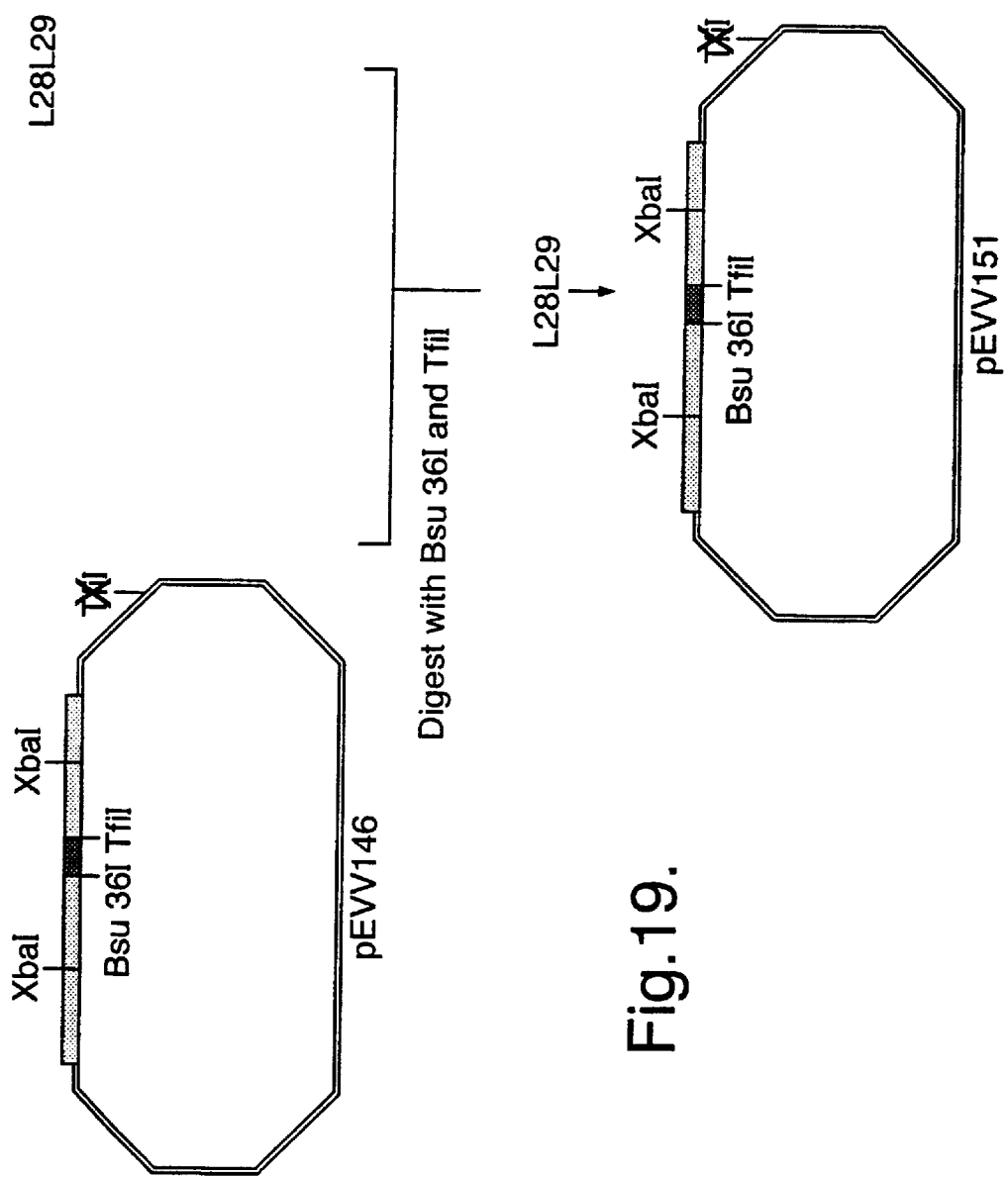
Figure 20:
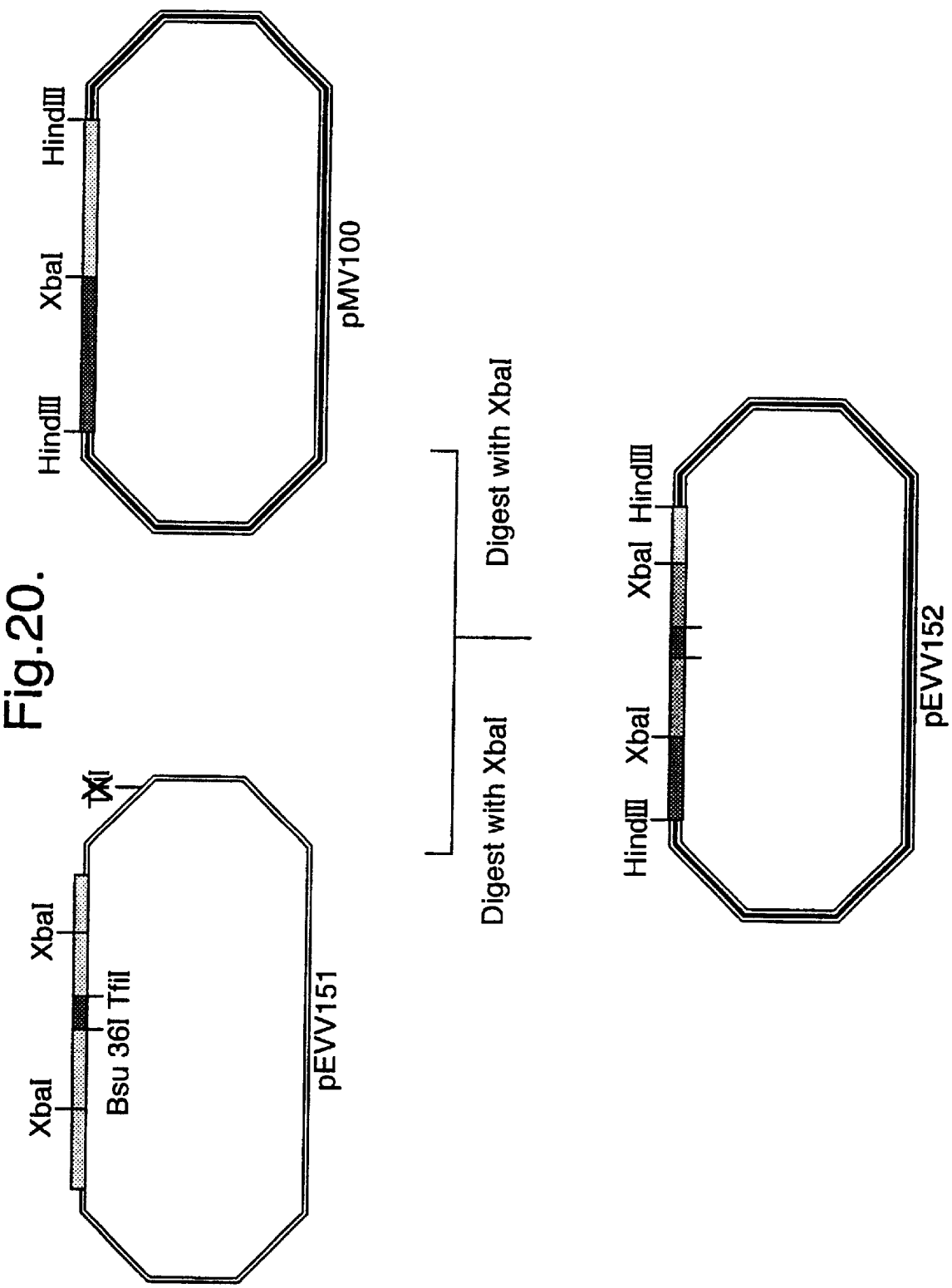

Core ΔNTS was generated by cloning the adapter L28L29 (FIG. 2f) into Bsu 36I-TfiI digested pEVV146 generating pEVV151 (FIG. 19). L28L29 contains nts7735 to 7750 which are adjacent to and continuous with the 42 from nt 7886 to 7921 The NTS is located between nt 7751 and 7885 therefore L28L29 encodes the region of the core gene between the Bsu 36I site and the NTS and the NTS and the TfiI site thus containing no sequence from the NTS and generating CAAΔNTS. CΔNTS was cloned into pMV100 from pEVV151 on an XbaI fragment generating pEVV152 (FIG. 20). The expression cassette containing the CΔNTS was subcloned from pEVV152 into pMV60 on a HindIII fragment generating pEVV153. RAd was generated using pEVV153.

Figure 21:
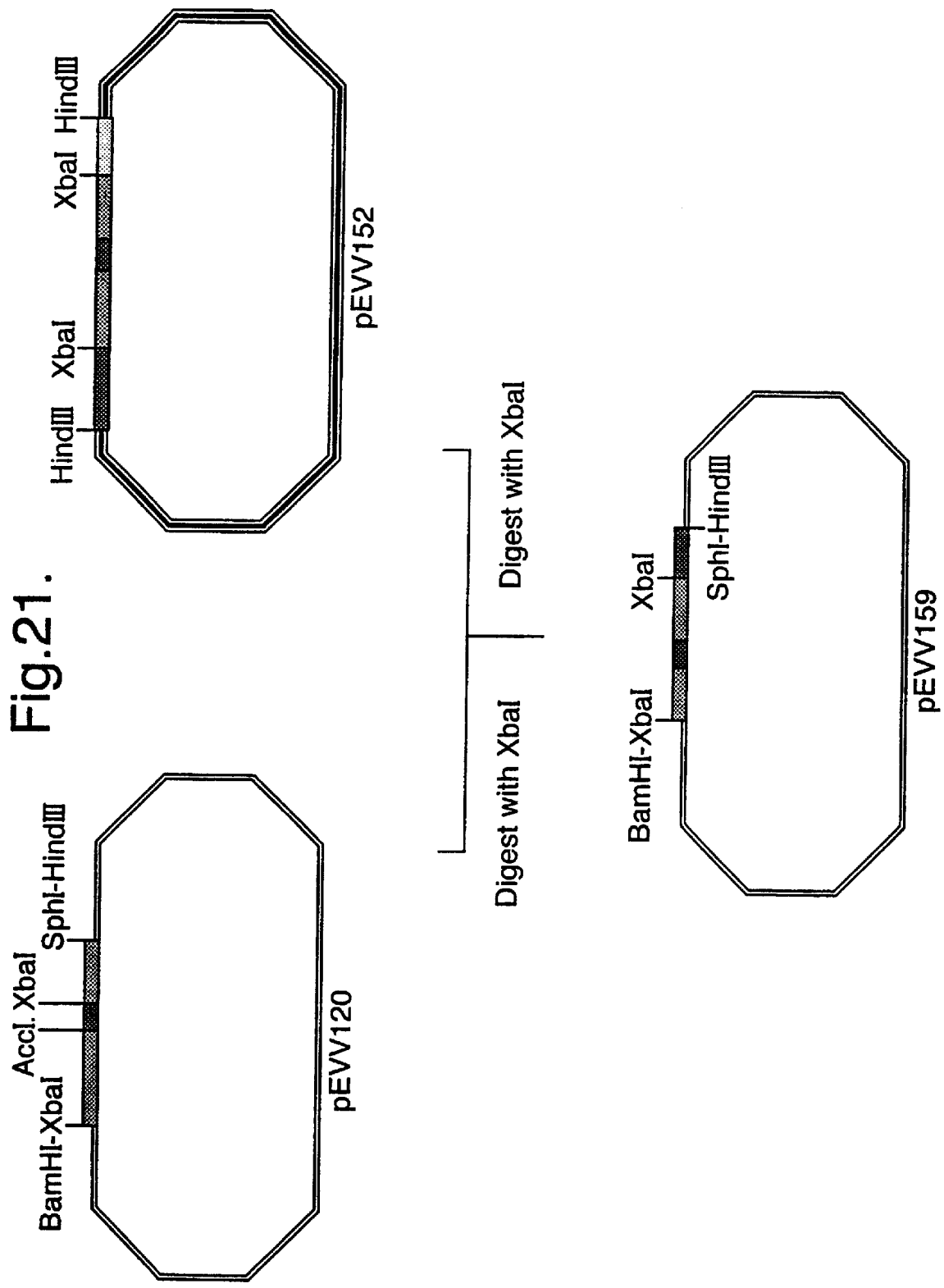
Figure 22:
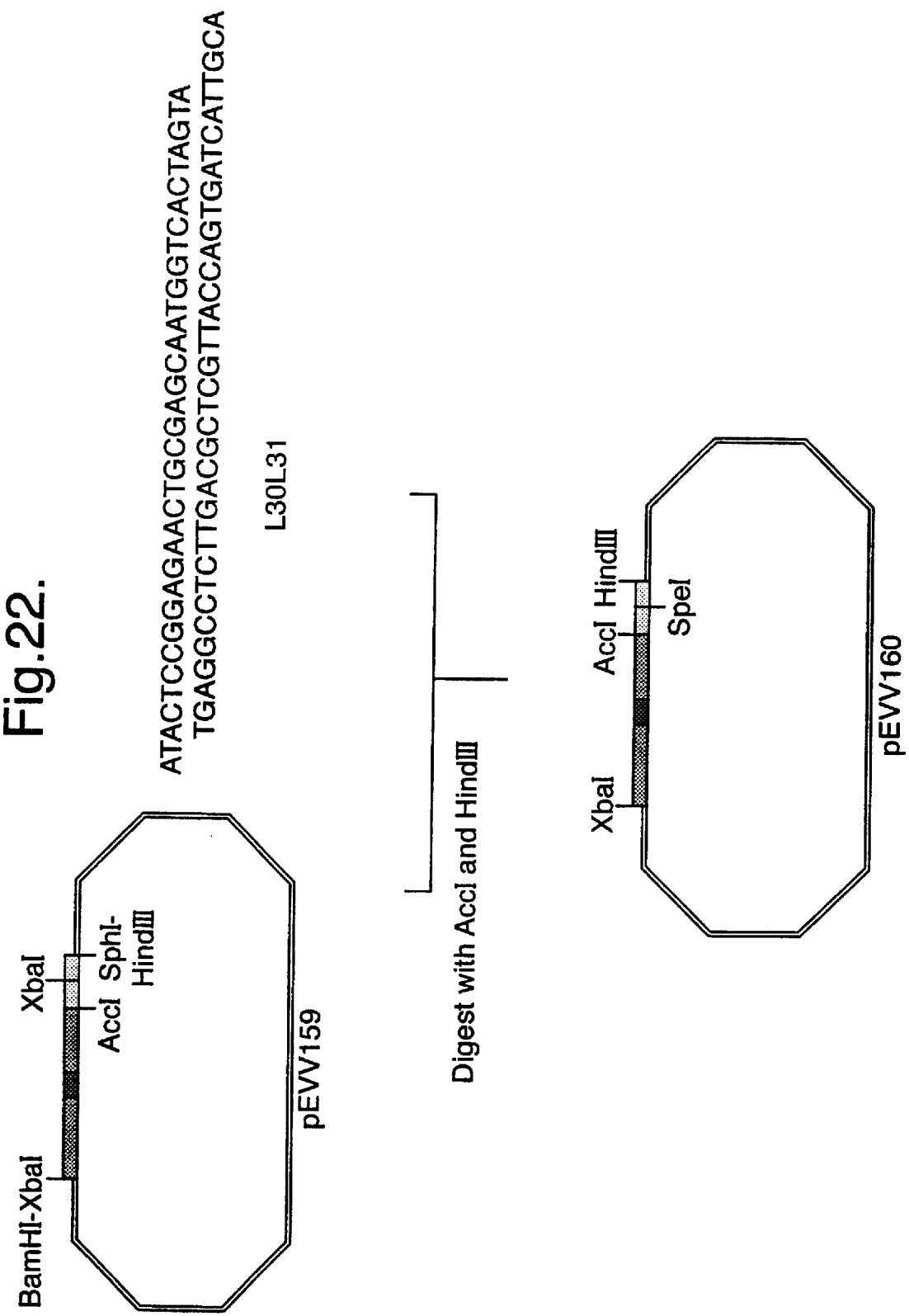
Figure 23:
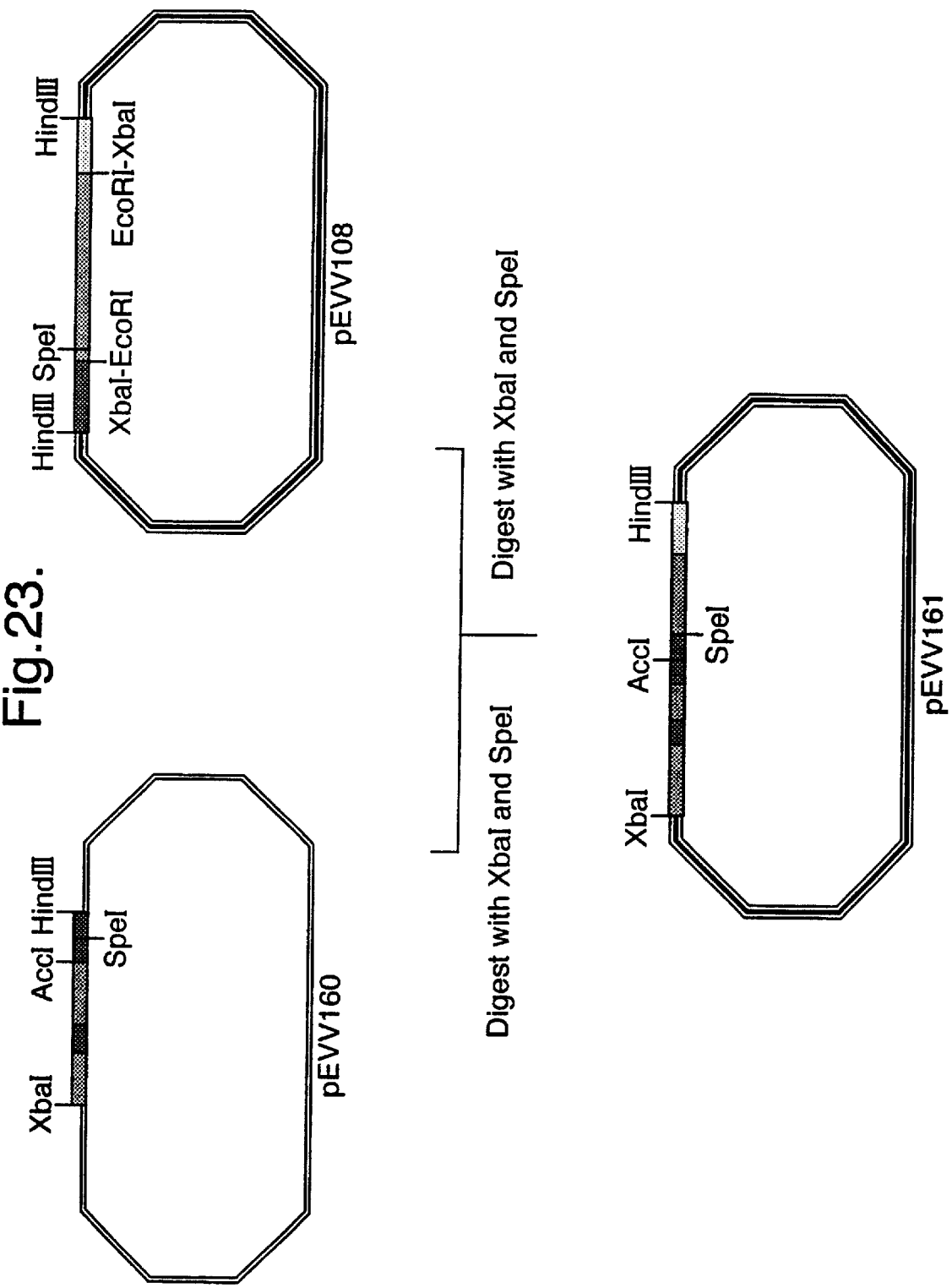
Figure 24:
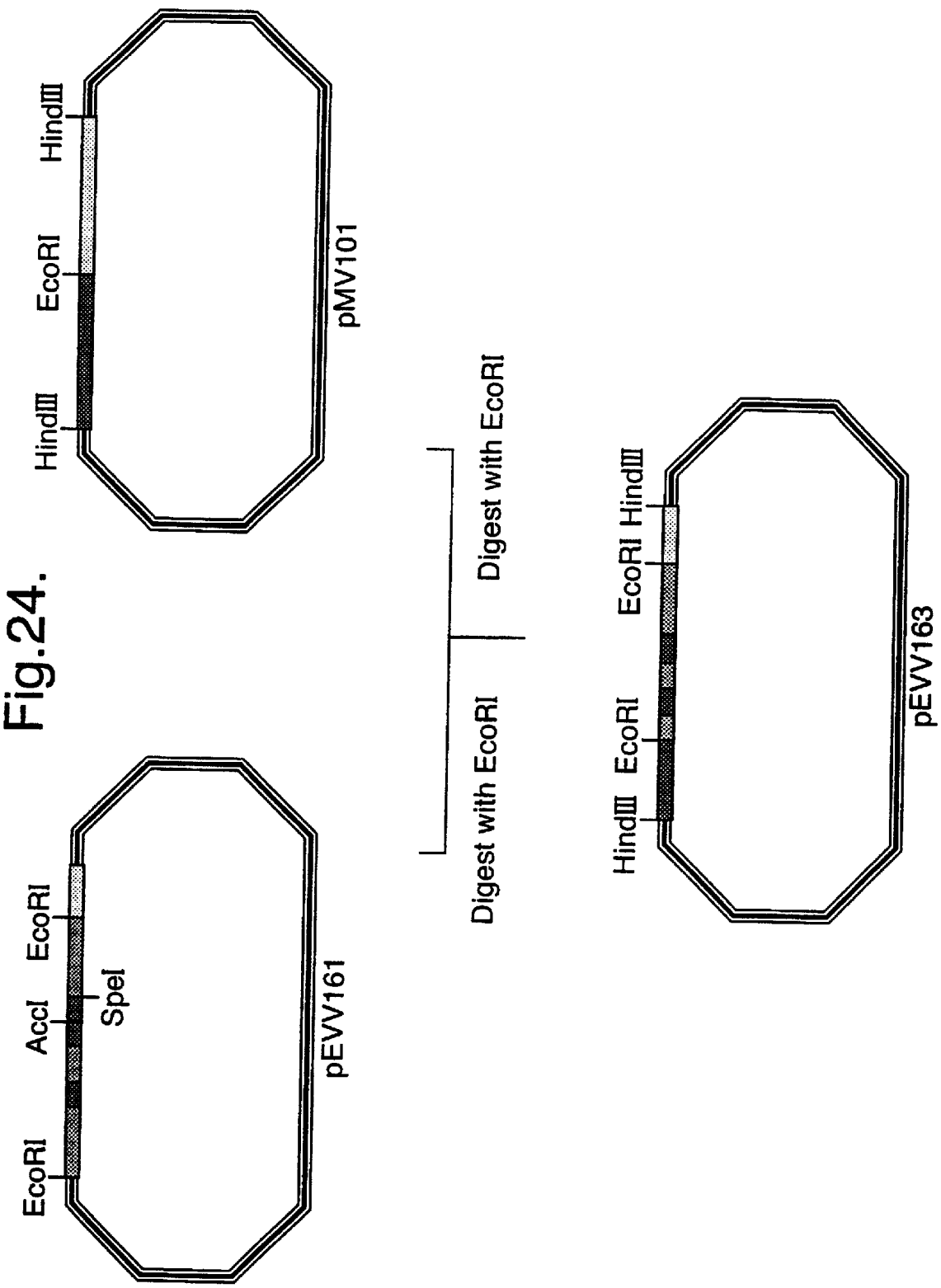

To confirm that the NTS encoded by core was responsible for the failure to generate recombinant adenovirus containing the VEEV core, CΔNTS was restored to the construct E3-E2-6K-E1-3' using adapter L30L31 (FIG. 2g). Adapter L30L31 contains the 34 nt downstream of the AccI site at nt8361 in core to nt 8394 of the SpeI site located in E1 and therefore rejoins core to E3. CDNTS was removed from pEVV152 on an XbaI fragment replacing 3'-C in pEVV120 generating pEVV159 (FIG. 21). L30L31 on a AccI-HindIII fragment was cloned into pEVV159 between the AccI site at the 3' of core and the HindIII site within the MCS of pEVV120 generating pEVV160 (FIG. 22). CDNTS+ L30L31 was removed from pEVV160 on XbaI-SpeI fragment and cloned into pEVV108 placing core-L30L31 upstream of E3 and restoring the Core-E3 junction generating pEVV161 (FIG. 23). The VEEV cDNA CΔNTS-E3-E2-6K-E1-3' was removed from pEVV160 on an EcoRI fragment and cloned into pEVV101 generating pEVV163 (FIG. 24). The expression cassette containing CΔNTS-E3-E2-6K-E1-3' was subcloned from pEVV163 into pMV60 on a HindIII fragment generating pEVV162. RAd was generated using pEVV162.

EXAMPLE 2

Confirmation of Nuclear Targeting Domain

Figure 25:
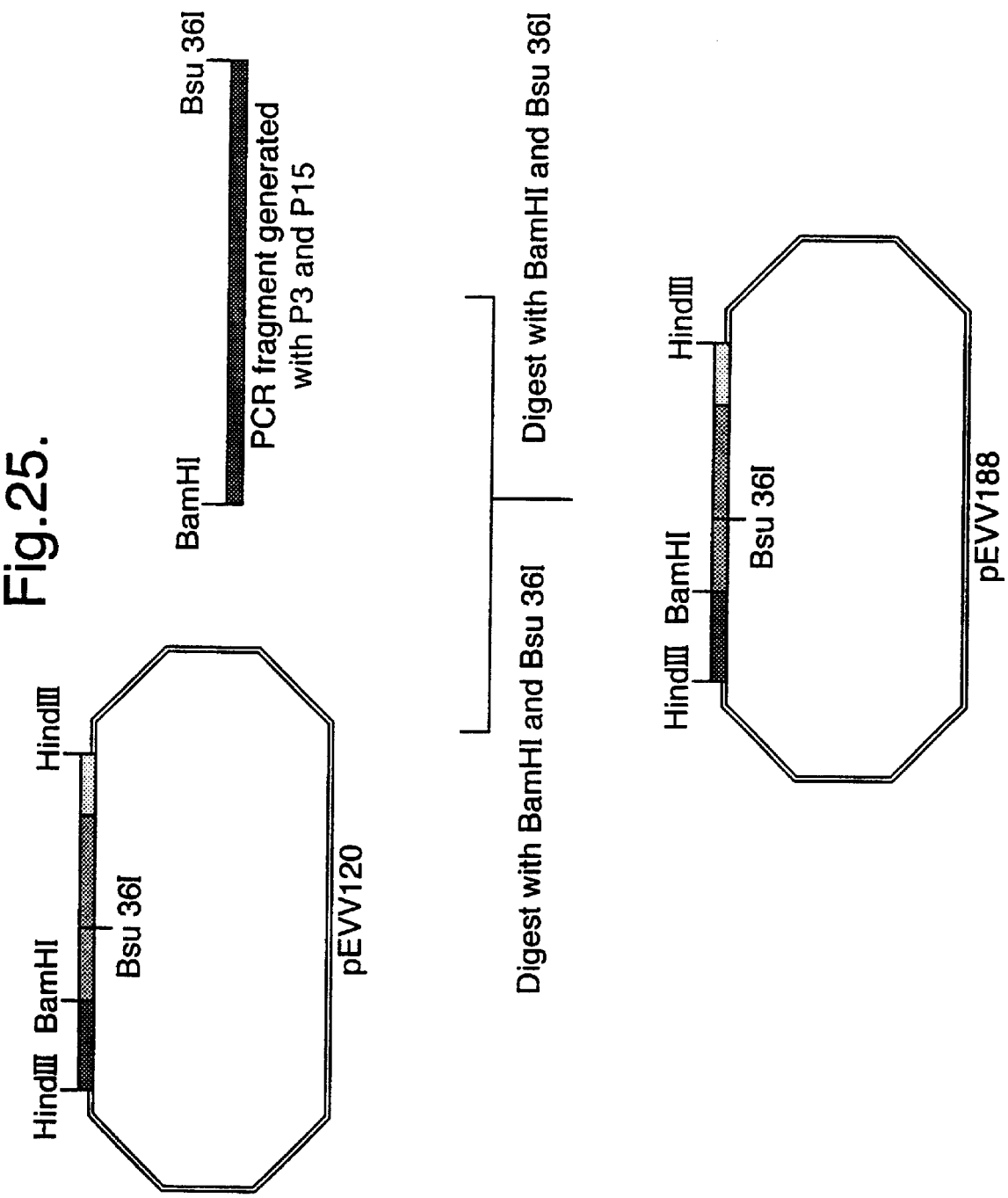

To determine the potential of the putative NTS to locate the Core protein to the cell nucleus, core was expressed as a fusion protein with Green Fluorescent Protein (GFP). The start codon (ATG) was removed from core by replacing the 5' of core in pEVV120 from the BamHI site immediately upstream of the start codon to the unique Bsu36I site within the core gene with a PCR fragment containing an identical fragment of core with the exception that the start codon had been removed. This PCR fragment was generated with the Primers P3 and P15. Within the primer P15 immediately upstream of the BamHI site and downstream of the first nucleotide of Core and additional two nucleotides were included (AT) in order to shift the reading frame two places to the right. This cloning generated the plasmid pEVV188 (FIG. 25).

Figure 26:
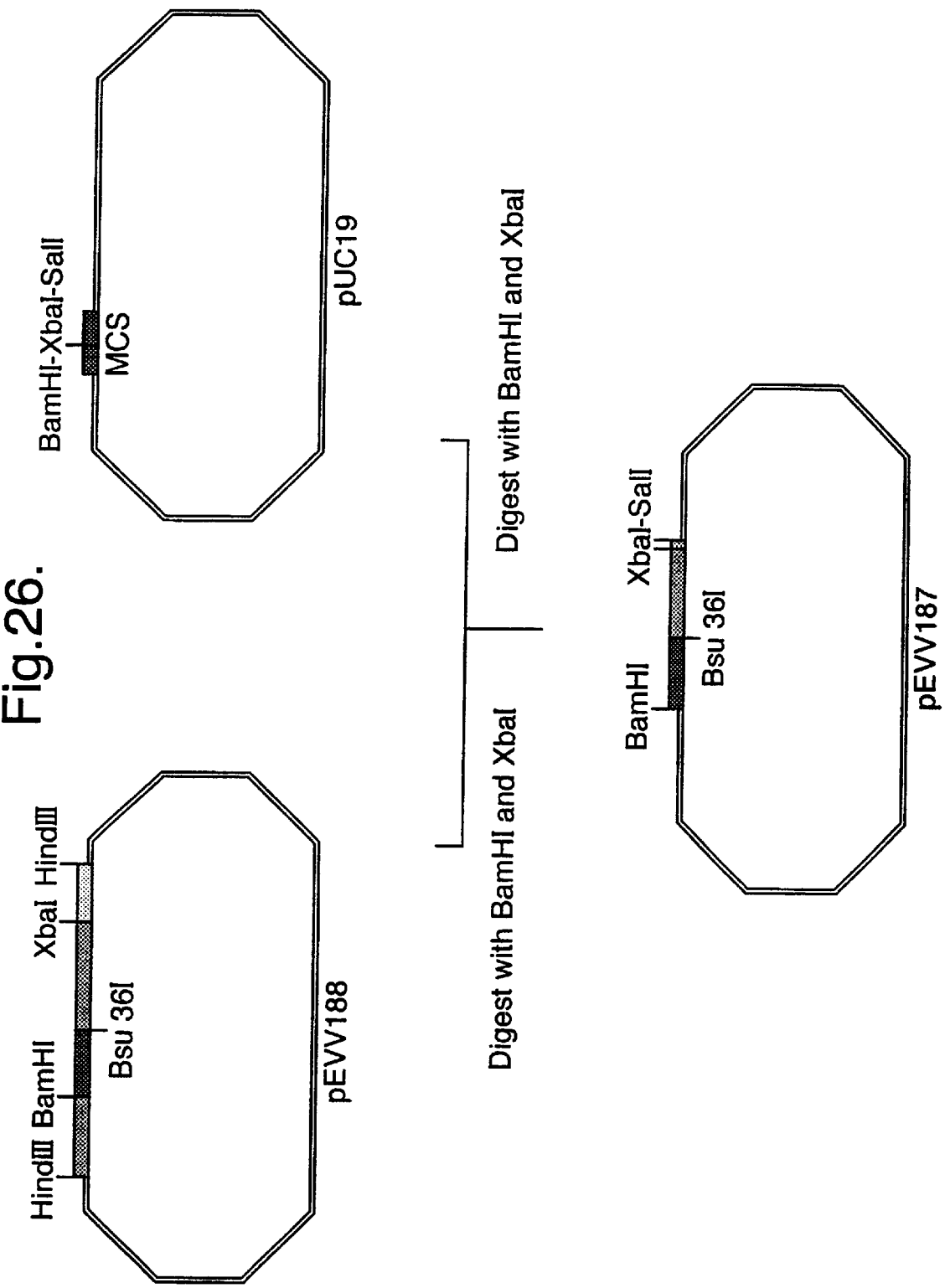
Figure 27:
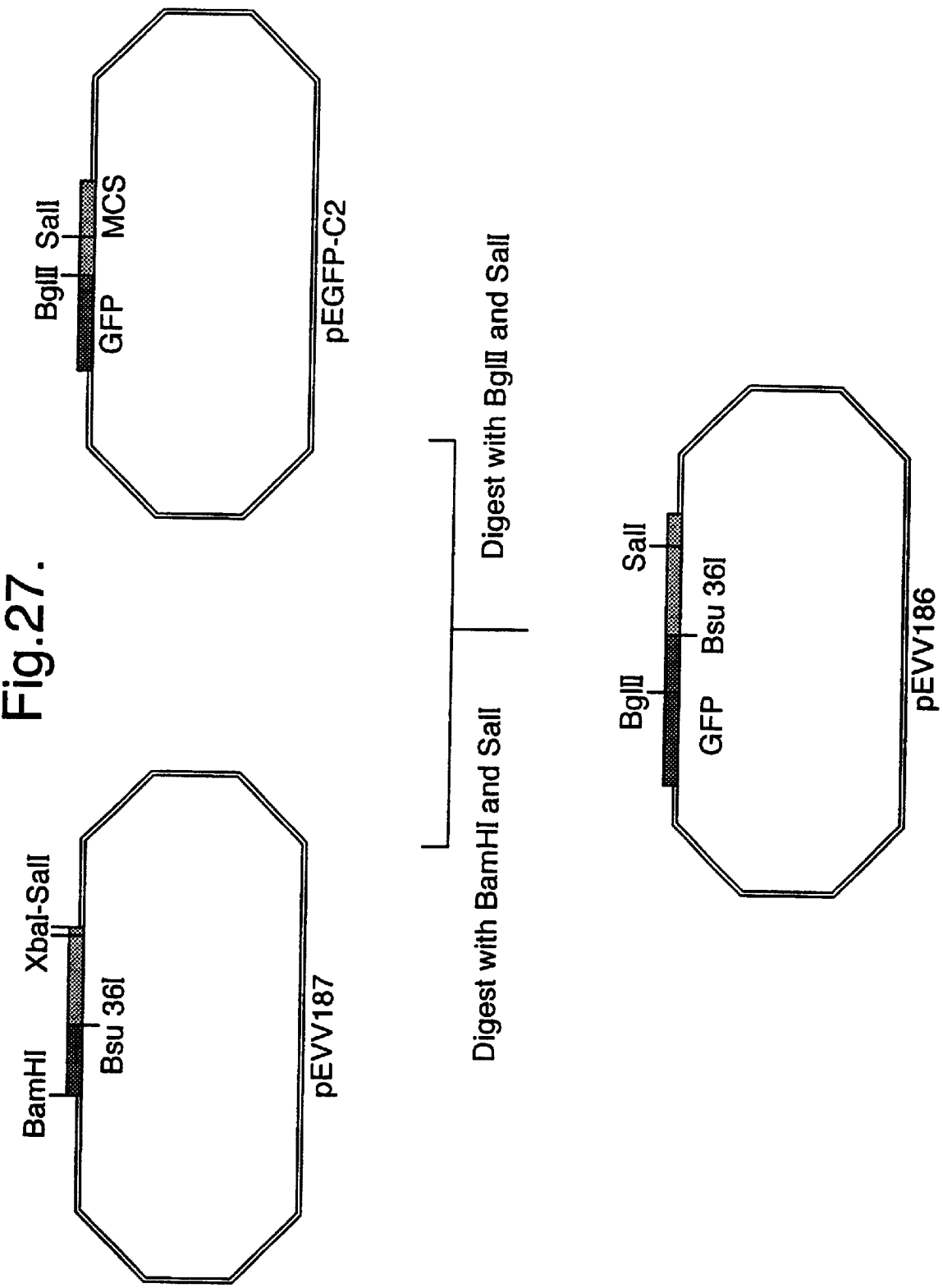

Core minus it's start codon was removed from pEVV188 on a BamHI-XbaI fragment and cloned into pUC19 generating pEVV187 (FIG. 26). This cloning placed a SalI site downstream of the XbaI site allowing core minus its start codon to be removed from pEVV187 on a BamHI-SalI fragment and cloned into the commercially available vector pEGFP-C2 (Clontech, Palo Alto Calif. USA) generating pEVV186 (FIG. 27). This cloning placed core minus its start codon downstream of and in frame with the GFP gene so that core is expressed as a C-terminal fusion with GFP.

When pEVV186 transfected cells were examined by immunofluorescence GFP was found to locate to the nucleus of the cell.

Figure 28:
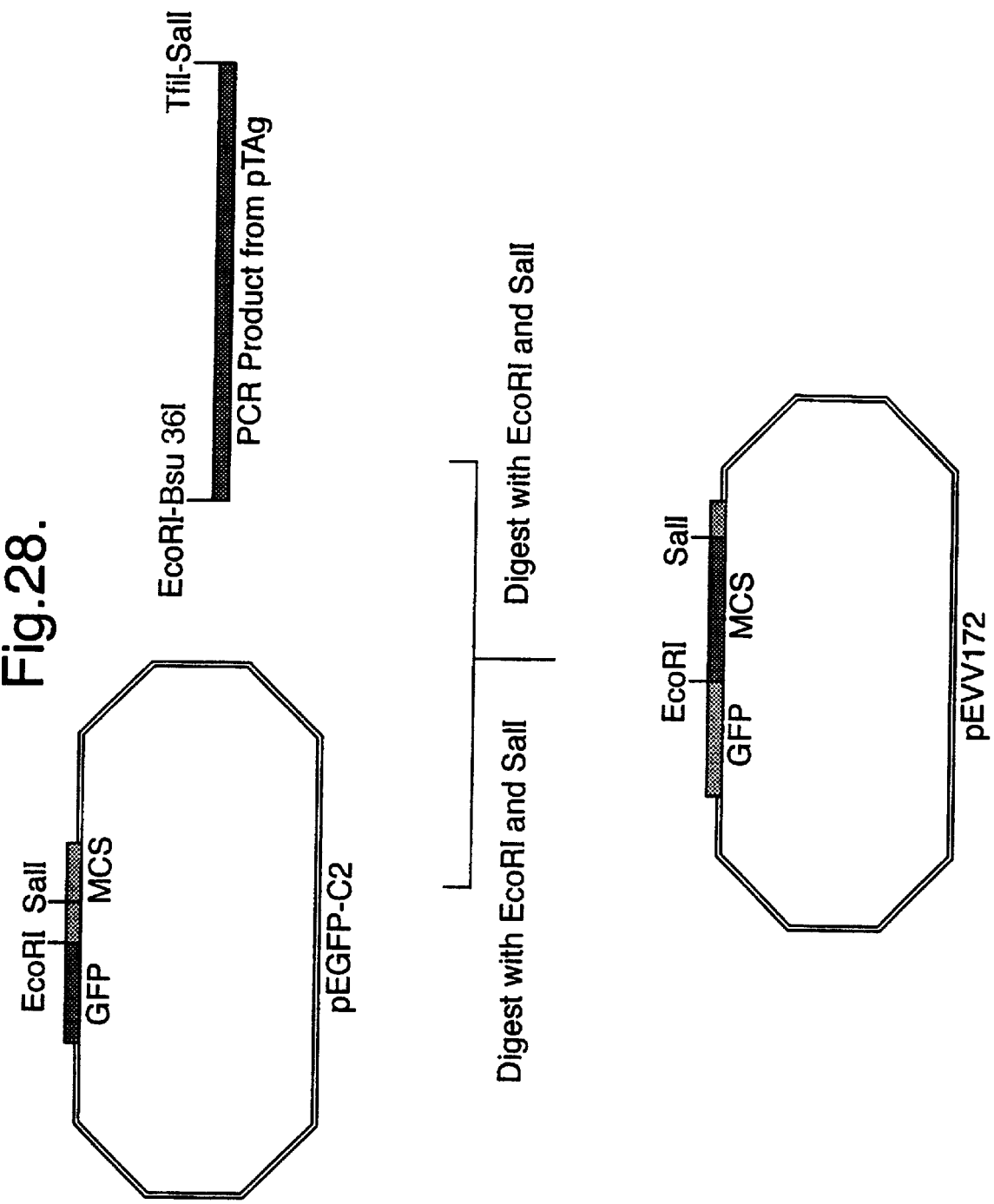

That targeting of GFP-core fusion protein to the nucleus was directed by the NTS encoded by core was demonstrated by generating pEVV172. pEVV172 (FIG. 28) was generated by cloning the NTS removed from pTAg (FIG. 17) on an EcoRI and SalI fragment and cloned into pEGFP-C2. The NTS was therefore expressed as a C-terminal fusion with GFP. A control plasmid pEVV173 was generated by removing the NTS on a BamHI and BglII fragment and cloning it back into pEGFP-C2 in the antisence orientation behind GFP. In cells transfected with pEvv173, GFP was located throughout the cell and particularly in the cytoplasm. In cells transfected with pEVV172, GFP was located to the nucleus.

EXAMPLE 3

Immunisation Studies

Groups of 10 balb/c mice were immunised with plasmids using the Helios Gene Gun (Bio-Rad, Hercules, Calif. USA). The plasmid used were pEVV100, pEVV102 and pEVV163. Each mouse received approximately 5 μg plasmid at day 0 and again after 11 weeks. Mice were then challenged 22 weeks following the original immunisation, with 30LD$_{50}$ of the virulent stain of VEEV TRD subcutaneously. The results are tabulated in table 1. This data suggests that the immune response elicited following immunisation with a plasmid pEVV163 elicited protection while pEVV102 did not. The protective effect seen appears not to be solely the result of an antibody response.

TABLE 1

| Plasmid | Number of mice surviving 20 days post challenge Total number of mice |
|---|---|
| pEVV100 | 0/10 |
| pEVV102 | 0/10 |
| pEVV163 | 3/10 |

What is claimed is:

1. A method for expressing alpha-virus polypeptide derived from an alpha virus: said method comprising transforming an adenovirus vector with a nucleic acid which encodes said alpha-virus polypeptide, wherein said alpha-virus polypeptide is comprised of at least one structural protein of said alpha virus and said alpha-virus polypeptide lacks a competent nuclear targeting signal of capsid protein of said alpha virus; and expressing said alpha-virus polypeptide.

2. A method according to claim 1, wherein said alpha-virus polypeptide has at least an amino acid sequence comprised of capsid-E3-E2 proteins of an alpha virus, and wherein said capsid-E3-E2 proteins lack a nuclear targeting signal.

3. A method according to claim 2, wherein said alpha-virus polypeptide has at least an amino acid sequence comprised of capsid-E3-E2-6K-E1 proteins of an alpha virus, and wherein said capsid-E3-E2-6K-E1 proteins lack a nuclear targeting signal.

4. A method according to claim 3, wherein said alpha-virus polypeptide does not contain an amino acid sequence corresponding to the amino acid sequence encoded by nucleotides 7749–7887 of Venezuelan Equine Encephalitis Virus.

5. A method according to claim 1, wherein said alpha virus is a Venezuelan Equine Encephalitis Virus (VEEV).

6. A method according to claim 5, wherein said alpha virus is VEEV and said nucleic acid lacks nucleotides 7749–7887 of the sequence thereof.

7. A method according to claim 5, wherein said nucleic acid has at least a nucleotide sequence comprised of cDNA encoding a VEEV protein which is cloned into said adenovirus vector in the antisense orientation.

8. A recombinant adenovirus vector which comprises a nucleic acid encoding an alpha-virus polypeptide which produces a protective immune response against an alpha virus in a mammal to whom it is administered, wherein said alpha-virus polypeptide is comprised of at least one structural protein of said alpha virus and said alpha-virus polypeptide lacks a competent nuclear targeting signal of capsid protein of said alpha virus; and wherein said adenovirus vector is capable of expressing said alpha-virus polypeptide.

9. A recombinant adenovirus vector according to claim 8, wherein said alpha-virus polypeptide has at least an amino acid sequence comprised of capsid-E3-E2 proteins of an alpha virus, and wherein said capsid-E3-E2 proteins lack a nuclear targeting signal.

10. A recombinant adenovirus vector according to claim 9, wherein said alpha-virus polypeptide has at least an amino acid sequence comprised of capsid-E3-E2-6K-E1 proteins of an alpha virus, and wherein said capsid-E3-E2-6K-E1 proteins lack a nuclear targeting signal.

11. A recombinant adenovirus vector according to claim 10, wherein said alpha-virus polypeptide does not contain an amino acid sequence corresponding to the amino acid sequence encoded by nucleotides 7749–7887 of Venezuelan Equine Encephalitis Virus.

12. A recombinant adenovirus vector according to claim 8, wherein said alpha virus is a Venezuelan Equine Encephalitis Virus (VEEV).

13. A recombinant adenovirus vector according to claim 12, wherein said alpha virus is VEEV and said nucleic acid lacks nucleotides 7749–7887 of the sequence thereof.

14. A recombinant adenovirus vector according to claim 12, wherein said nucleic acid has at least a nucleotide sequence comprised of cDNA encoding a VEEV protein which is cloned into said adenovirus vector in the antisense orientation.

15. A vaccine which comprises a recombinant adenovirus vector according to claim 8.

16. A vaccine according to claim 15 which further comprises a pharmaceutically acceptable carrier.

17. A method of producing a protective immune response to an alpha virus in a mammal, said method comprising administering to said mammal a recombinant adenovirus according to claim 8.

18. A method according to claim 17, wherein said alpha-virus polypeptide has at least an amino acid sequence comprised of capsid-E3-E2 proteins of an alpha virus, and wherein said capsid-E3-E2 proteins lack a nuclear targeting signal.

19. A method according to claim 18, wherein said alpha-virus polypeptide has at least an amino acid sequence comprised of capsid-E3-E26K-E1 proteins of an alpha virus, and wherein said capsid-E3-E26K-E1 proteins lack a nuclear targeting signal.

20. A method according to claim 19, wherein said alpha-virus polypeptide does not contain an amino acid sequence corresponding to the amino acid sequence encoded by nucleotides 7749–7887 of Venezuelan Equine Encephalitis Virus.

21. A method according to claim 17, wherein said alpha virus is a Venezuelan Equine Encephalitis Virus (VEEV).

22. A method according to claim 21, wherein said alpha virus is VEEV and said nucleic acid lacks nucleotides 7749–7887 of the sequence thereof.

23. A method according to claim 21, wherein said nucleic acid has at least a nucleotide sequence comprised of cDNA encoding a VEEV protein which is cloned into said adenovirus vector in the antisense orientation.

* * * * *

SEQUENCE LISTING

<160> NUMBER OF SEQ ID NOS: 18

<210> SEQ ID NO 1
<211> LENGTH: 12
<212> TYPE: DNA
<213> ORGANISM: Artificial Sequence
<220> FEATURE:
<223> OTHER INFORMATION: L1 adapter upper strand

<400> SEQUENCE: 1
ctagagaatt ct                                                            12

<210> SEQ ID NO 2
<211> LENGTH: 12
<212> TYPE: DNA
<213> ORGANISM: Artificial Sequence
<220> FEATURE:
<223> OTHER INFORMATION: L1 adapter lower strand

<400> SEQUENCE: 2
ctagagaatt ct                                                            12

<210> SEQ ID NO 3
<211> LENGTH: 28
<212> TYPE: DNA
<213> ORGANISM: Artificial Sequence
<220> FEATURE:
<223> OTHER INFORMATION: L4A adapter upper strand

<400> SEQUENCE: 3
ctagtgacat ggtgaattca ccatgtca                                           28

<210> SEQ ID NO 4
<211> LENGTH: 28
<212> TYPE: DNA
<213> ORGANISM: Artificial Sequence
<220> FEATURE:
<223> OTHER INFORMATION: L4A adapter lower strand

<400> SEQUENCE: 4
ctagtgacat ggtgaattca ccatgtca                                           28

<210> SEQ ID NO 5
<211> LENGTH: 22
<212> TYPE: DNA
<213> ORGANISM: Artificial Sequence
<220> FEATURE:
<223> OTHER INFORMATION: L7L8 adapter upper strand

<400> SEQUENCE: 5
gatccgtata ctctagagca tg                                                 22

<210> SEQ ID NO 6
<211> LENGTH: 14
<212> TYPE: DNA
<213> ORGANISM: Artificial Sequence
<220> FEATURE:
<223> OTHER INFORMATION: L7L8 adapter lower strand

<400> SEQUENCE: 6
ctctagagta tacg                                                          14

<210> SEQ ID NO 7
<211> LENGTH: 30

```
<212> TYPE: DNA
<213> ORGANISM: Artificial Sequence
<220> FEATURE:
<223> OTHER INFORMATION: L5L6 adapter upper strand

<400> SEQUENCE: 7
atactccgga gaactgcgag caatggtaat                                30

<210> SEQ ID NO 8
<211> LENGTH: 32
<212> TYPE: DNA
<213> ORGANISM: Artificial Sequence
<220> FEATURE:
<223> OTHER INFORMATION: L5L6 adapter lower strand

<400> SEQUENCE: 8
ctagattacc attgctcgca gttctccgga gt                             32

<210> SEQ ID NO 9
<211> LENGTH: 17
<212> TYPE: DNA
<213> ORGANISM: Artificial Sequence
<220> FEATURE:
<223> OTHER INFORMATION: L10L13 adapter upper strand

<400> SEQUENCE: 9
ttaatctaga agatgca                                              17

<210> SEQ ID NO 10
<211> LENGTH: 17
<212> TYPE: DNA
<213> ORGANISM: Artificial Sequence
<220> FEATURE:
<223> OTHER INFORMATION: L10L13 adapter lower strand

<400> SEQUENCE: 10
tcttctagat taatgca                                              17

<210> SEQ ID NO 11
<211> LENGTH: 59
<212> TYPE: DNA
<213> ORGANISM: Artificial Sequence
<220> FEATURE:
<223> OTHER INFORMATION: L28L29 adapter upper strand

<400> SEQUENCE: 11
tgaggggcca tccgctaaca agaaaccagg caagagacag cgcatggtca tgaaattgg    59

<210> SEQ ID NO 12
<211> LENGTH: 59
<212> TYPE: DNA
<213> ORGANISM: Artificial Sequence
<220> FEATURE:
<223> OTHER INFORMATION: L28L29 adapter lower strand

<400> SEQUENCE: 12
attccaattt catgaccatg cgctgtctct tgcctggttt cttgttagcg gatggcccc    59

<210> SEQ ID NO 13
<211> LENGTH: 35
<212> TYPE: DNA
<213> ORGANISM: Artificial Sequence
<220> FEATURE:
<223> OTHER INFORMATION: L30L31 adapter upper strand

<400> SEQUENCE: 13
```

```
                                        -continued atactccgga gaactgcgag caatggtcac tagta                              35

<210> SEQ ID NO 14
<211> LENGTH: 37
<212> TYPE: DNA
<213> ORGANISM: Artificial Sequence
<220> FEATURE:
<223> OTHER INFORMATION: L30L31 adapter lower strand

<400> SEQUENCE: 14
acgttactag tgaccattgc tcgcagttct ccggagt                            37

<210> SEQ ID NO 15
<211> LENGTH: 29
<212> TYPE: DNA
<213> ORGANISM: Artificial Sequence
<220> FEATURE:
<223> OTHER INFORMATION: P2 primer

<400> SEQUENCE: 15
ggccggatcc ggatgttccc gttccagcc                                     29

<210> SEQ ID NO 16
<211> LENGTH: 24
<212> TYPE: DNA
<213> ORGANISM: Artificial Sequence
<220> FEATURE:
<223> OTHER INFORMATION: P3 primer

<400> SEQUENCE: 16
gcgcggatcc cctcaggtgg cgcg                                          24

<210> SEQ ID NO 17
<211> LENGTH: 22
<212> TYPE: DNA
<213> ORGANISM: Artificial Sequence
<220> FEATURE:
<223> OTHER INFORMATION: L20 primer

<400> SEQUENCE: 17
gcgccactga ggggccatcc gc                                            22

<210> SEQ ID NO 18
<211> LENGTH: 34
<212> TYPE: DNA
<213> ORGANISM: Artificial Sequence
<220> FEATURE:
<223> OTHER INFORMATION: L21 primer

<400> SEQUENCE: 18
cggggattct ggtttcttgt tggtcttctt cttg                               34
```